(12) United States Patent
Lenker

(10) Patent No.: US 11,819,642 B2
(45) Date of Patent: Nov. 21, 2023

(54) STEERABLE GUIDEWIRE AND METHOD OF USE

(71) Applicant: Indian Wells Medical, Inc., Lake Forest, CA (US)

(72) Inventor: Jay A. Lenker, Lake Forest, CA (US)

(73) Assignee: Indian Wells Medical, Inc., Lake Forest, CA (US)

( * ) Notice: Subject to any disclaimer, the term of this patent is extended or adjusted under 35 U.S.C. 154(b) by 319 days.

(21) Appl. No.: 17/034,928

(22) Filed: Sep. 28, 2020

(65) Prior Publication Data

US 2021/0008353 A1    Jan. 14, 2021

Related U.S. Application Data

(63) Continuation of application No. 15/454,924, filed on Mar. 9, 2017, now Pat. No. 10,786,655.

(60) Provisional application No. 62/307,691, filed on Mar. 14, 2016.

(51) Int. Cl.
*A61M 25/09* (2006.01)

(52) U.S. Cl.
CPC ...... *A61M 25/09041* (2013.01); *A61M 25/09025* (2013.01); *A61M 2025/09116* (2013.01)

(58) Field of Classification Search
CPC ...... A61M 25/09041; A61M 25/09025; A61M 25/09116
See application file for complete search history.

(56) References Cited

U.S. PATENT DOCUMENTS

| 3,802,440 A | 4/1974 | Salem |
| 4,757,827 A | 7/1988 | Buchbinder et al. |
| 4,815,478 A | 3/1989 | Buchbinder et al. |

(Continued)

FOREIGN PATENT DOCUMENTS

| EP | 1898801 | 3/2008 |
| JP | 2004508147 | 3/2004 |

(Continued)

OTHER PUBLICATIONS

Examiner's Report and Examination Search Report from Canadian Patent Application No. 2,870,854 dated Nov. 7, 2019.

(Continued)

*Primary Examiner* — Marjan Fardanesh
(74) *Attorney, Agent, or Firm* — Crockett & Crockett, PC; K. David Crockett, Esq.

(57) ABSTRACT

This invention is a transvascularly placed steerable guidewire, further including internal steerability and the ability to articulate in a direction at right angles to its longitudinal axis at or near its distal end. The steerable guidewire is generally fabricated from stainless steel and includes an outer tube, an inner tube, hub structures, and a distal articulating region. The steerable guidewire can be advanced through a body lumen in its straight configuration and then be selectively articulated or curved to permit negotiation of tortuous curvature. The steerable guidewire hub can be removed to permit advancement of catheters over its proximal end followed by re-attachment of the hub to permit deflection of the distal end of the steerable guidewire. Removal of the hub can result in a limp guidewire or maintenance of a forced curvature of the distal end of the guidewire.

12 Claims, 19 Drawing Sheets

(56) References Cited

U.S. PATENT DOCUMENTS

| | | |
|---|---|---|
| 5,725,512 A | 3/1998 | Swartz et al. |
| 6,136,016 A | 10/2000 | Barbut et al. |
| 6,217,527 B1 | 4/2001 | Selmon et al. |
| 6,419,641 B1 | 7/2002 | Mark et al. |
| 6,650,923 B1 | 11/2003 | Lesh |
| 6,695,814 B2 | 2/2004 | Greene et al. |
| 7,471,697 B2 | 12/2008 | Kamiya et al. |
| 7,488,448 B2 | 2/2009 | Wieting et al. |
| 7,615,044 B2 | 11/2009 | Scheibe |
| 7,632,277 B2 | 12/2009 | Woll |
| 7,678,081 B2 | 3/2010 | Whiting et al. |
| 7,824,356 B2 | 11/2010 | Wieting et al. |
| 7,935,102 B2 | 5/2011 | Breznock et al. |
| 8,235,943 B2 | 8/2012 | Breznock et al. |
| 8,323,241 B2 | 12/2012 | Salahieh et al. |
| 8,480,606 B2 | 7/2013 | Wieting et al. |
| 8,491,619 B2 | 7/2013 | Breznock |
| 8,939,926 B2 | 1/2015 | Wieting et al. |
| 8,961,550 B2 | 2/2015 | Lenker et al. |
| 9,445,836 B2 | 9/2016 | Breznock |
| 9,555,182 B2 | 1/2017 | Wieting et al. |
| 9,707,007 B2 | 7/2017 | Lenker et al. |
| 9,993,266 B2 | 6/2018 | Lenker et al. |
| 10,016,210 B2 | 7/2018 | Enker et al. |
| 10,016,221 B2 | 7/2018 | Lenker et al. |
| 10,034,686 B2 | 7/2018 | Breznock |
| 10,369,265 B2 | 8/2019 | Wieting et al. |
| 10,485,569 B2 | 11/2019 | Lenker et al. |
| 10,485,579 B2 | 11/2019 | Lenker |
| 10,729,457 B2 | 8/2020 | Lenker et al. |
| 10,779,858 B2 | 9/2020 | Lenker et al. |
| 10,786,655 B2 | 9/2020 | Lenker |
| 10,806,483 B2 | 10/2020 | Breznock |
| 10,932,815 B1 | 3/2021 | Lenker et al. |
| 11,090,080 B2 | 8/2021 | Lenker et al. |
| 11,234,728 B2 | 2/2022 | Lenker et al. |
| 11,317,938 B2 | 5/2022 | Lenker et al. |
| 11,382,654 B2 | 7/2022 | Lenker |
| 11,490,922 B2 | 11/2022 | Lenker et al. |
| 2004/0193073 A1 | 9/2004 | DeMello et al. |
| 2004/0267361 A1 | 12/2004 | Donnelly et al. |
| 2005/0004515 A1 | 1/2005 | Hart et al. |
| 2005/0101984 A1 | 5/2005 | Chanduszko et al. |
| 2005/0267495 A1 | 12/2005 | Ginn et al. |
| 2006/0074442 A1 | 4/2006 | Noriega et al. |
| 2007/0060878 A1 | 3/2007 | Bonnette et al. |
| 2008/0045863 A1 | 2/2008 | Bakos |
| 2008/0045908 A1 | 2/2008 | Gould et al. |
| 2008/0243081 A1 | 10/2008 | Nance |
| 2009/0036832 A1 | 2/2009 | Skujins et al. |
| 2010/0185053 A1 | 7/2010 | Hagen |
| 2010/0228276 A1 | 9/2010 | Breznock |
| 2011/0245615 A1 | 10/2011 | Iwasake et al. |
| 2011/0245800 A1 | 10/2011 | Kassab et al. |
| 2011/0319905 A1 | 12/2011 | Palme et al. |
| 2014/0343538 A1* | 11/2014 | Lenker ............... A61B 17/3417 604/528 |
| 2018/0317949 A1 | 11/2018 | Lenker et al. |

FOREIGN PATENT DOCUMENTS

| | | |
|---|---|---|
| WO | WO9513752 | 5/1995 |
| WO | WO0064525 | 11/2000 |
| WO | WO2007-035497 | 3/2007 |
| WO | WO2007-115314 | 10/2007 |
| WO | WO2008069772 | 6/2008 |
| WO | WO2009112060 | 9/2009 |
| WO | WO2010151698 | 12/2010 |

OTHER PUBLICATIONS

Office Action dated Jul. 19, 2018 from European Patent Application No. 13861154.6.

International Search Report dated Jul. 18, 2013 from PCT Application PCT/US2013/034474.

Search Report dated May 16, 2013 from GB Application GB1308015.5.

International Search Report dated Mar. 6, 2014 from PCT Application PCT/US2013/073262.

Extended European Search Report dated Aug. 4, 2015 from EP Application 13778011.0.

Extended European Search Report dated Jun. 16, 2016 from European Patent Application 13861154.6.

Office Action dated Feb. 23, 2017 from Chinese Patent Application No. 201380072336.2.

Examination Report dated Oct. 6, 2017 from European Patent Application No. 13861154.6.

Notification of Reasons for Refusal dated Oct. 24, 2017 from Japanese Patent Application No. 2015545833.

* cited by examiner

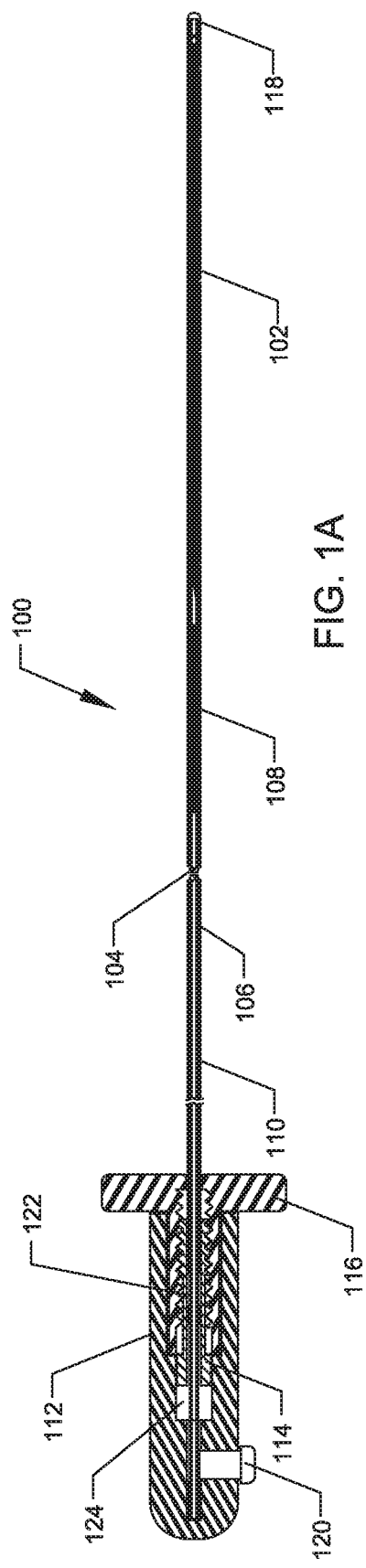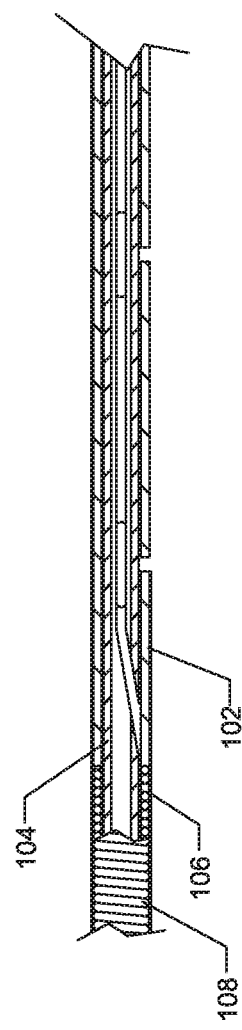

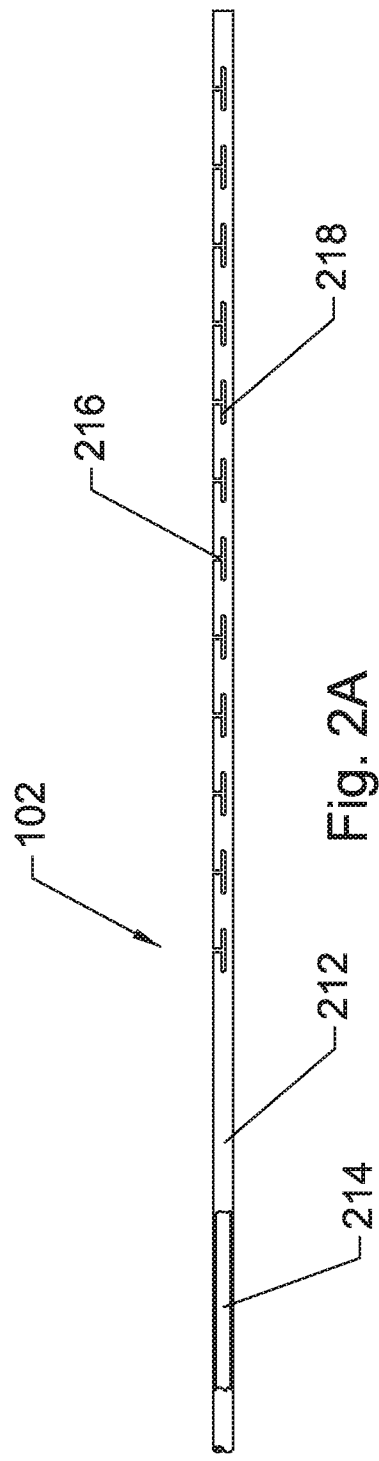
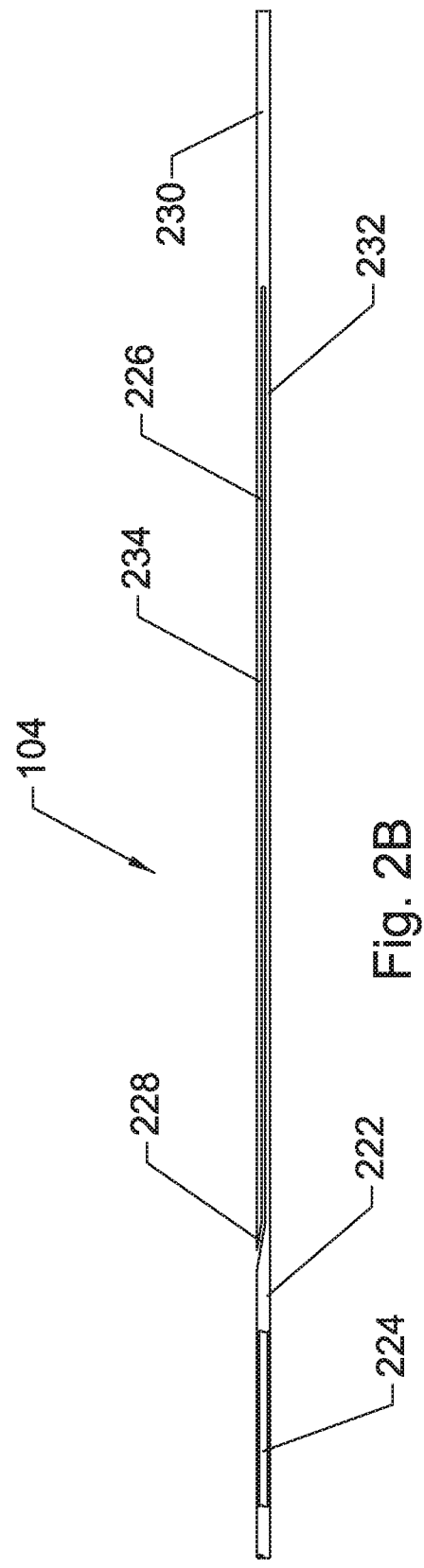

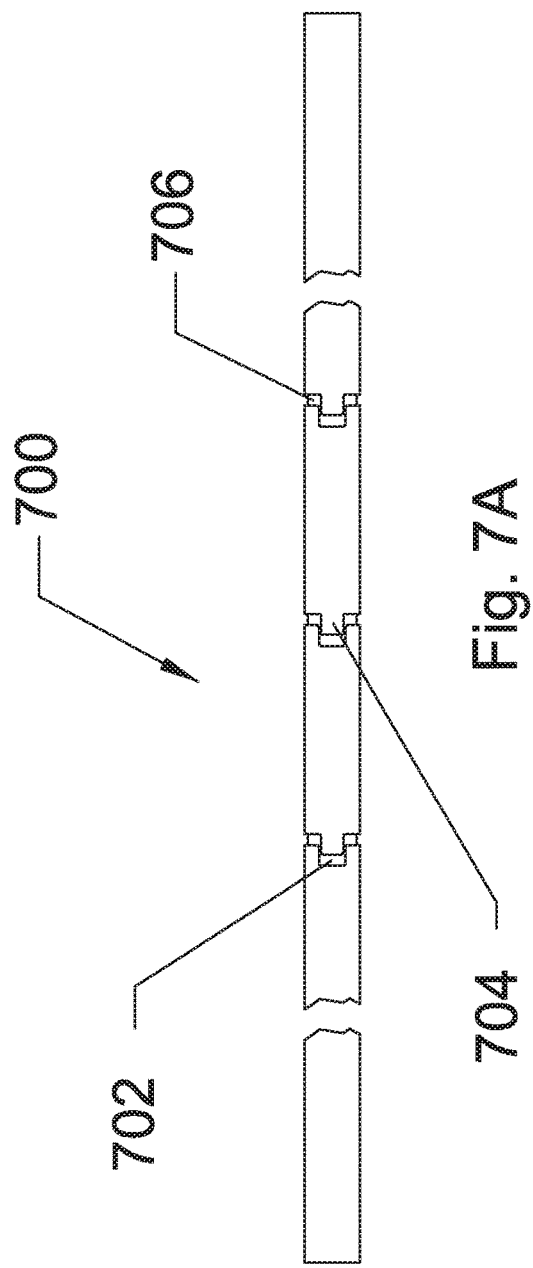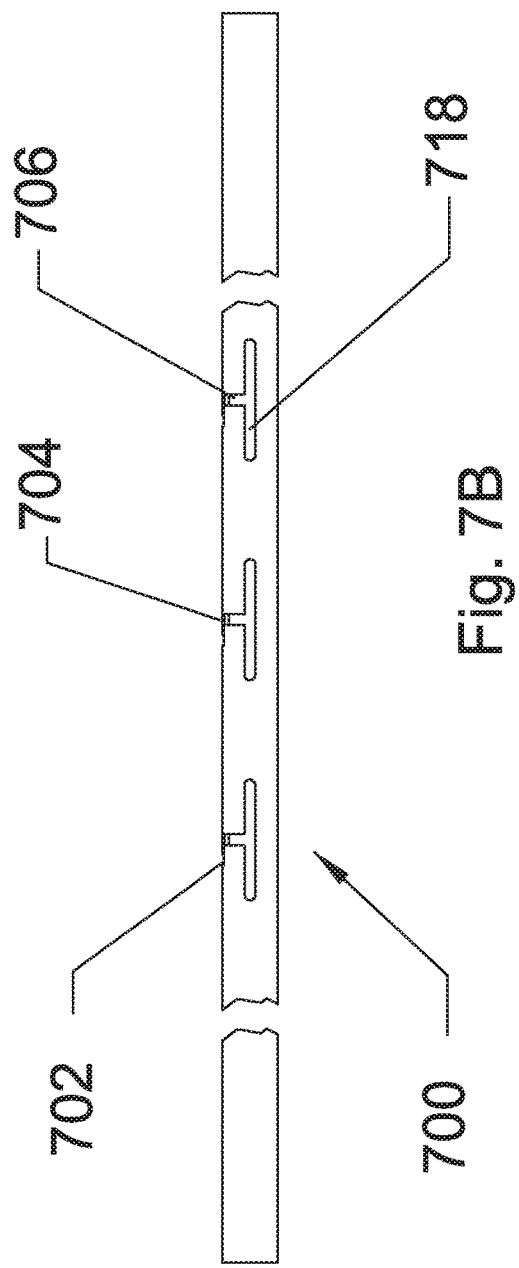

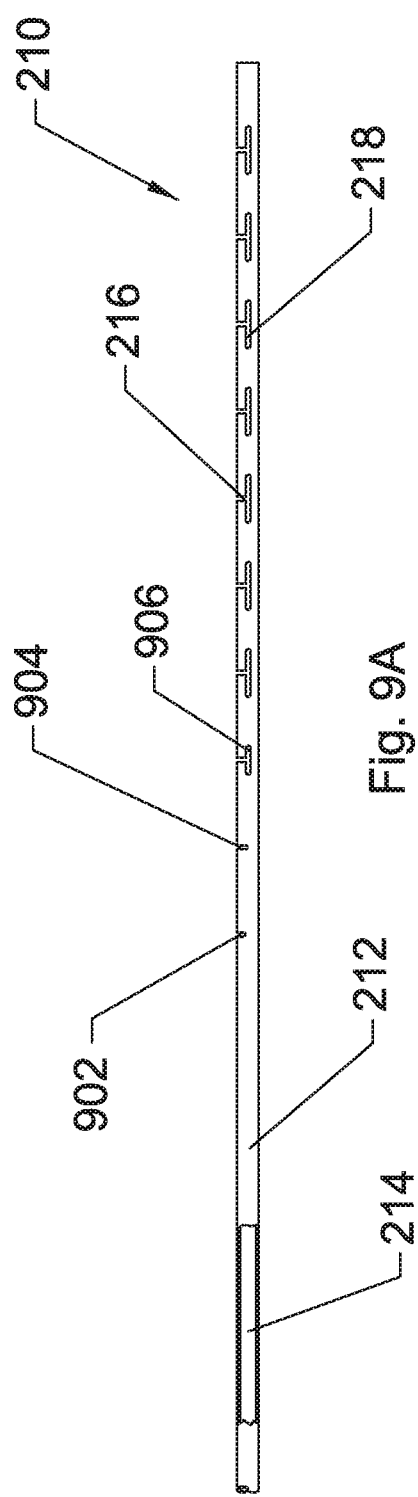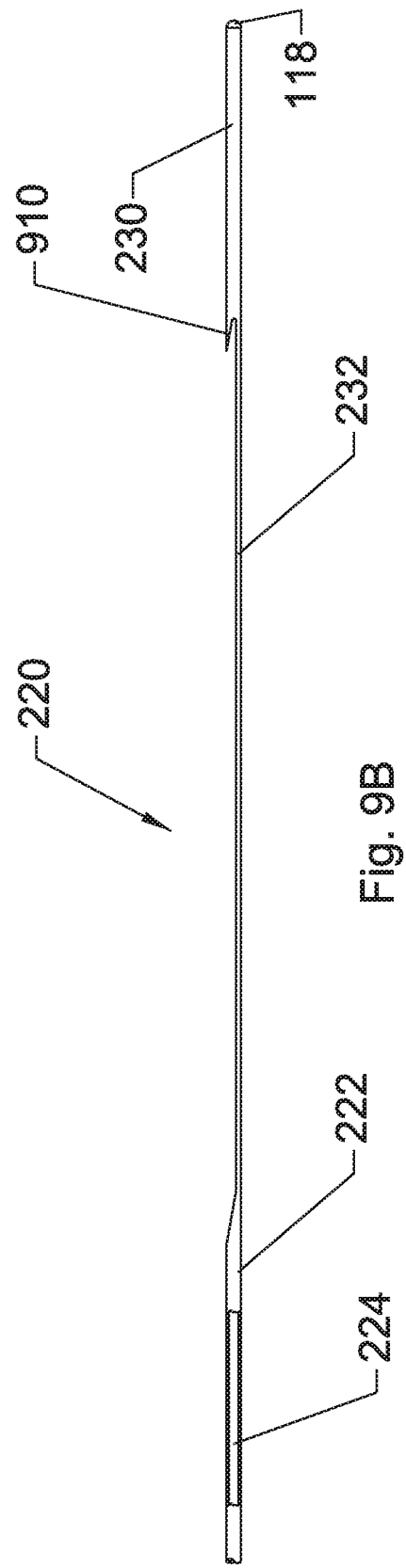

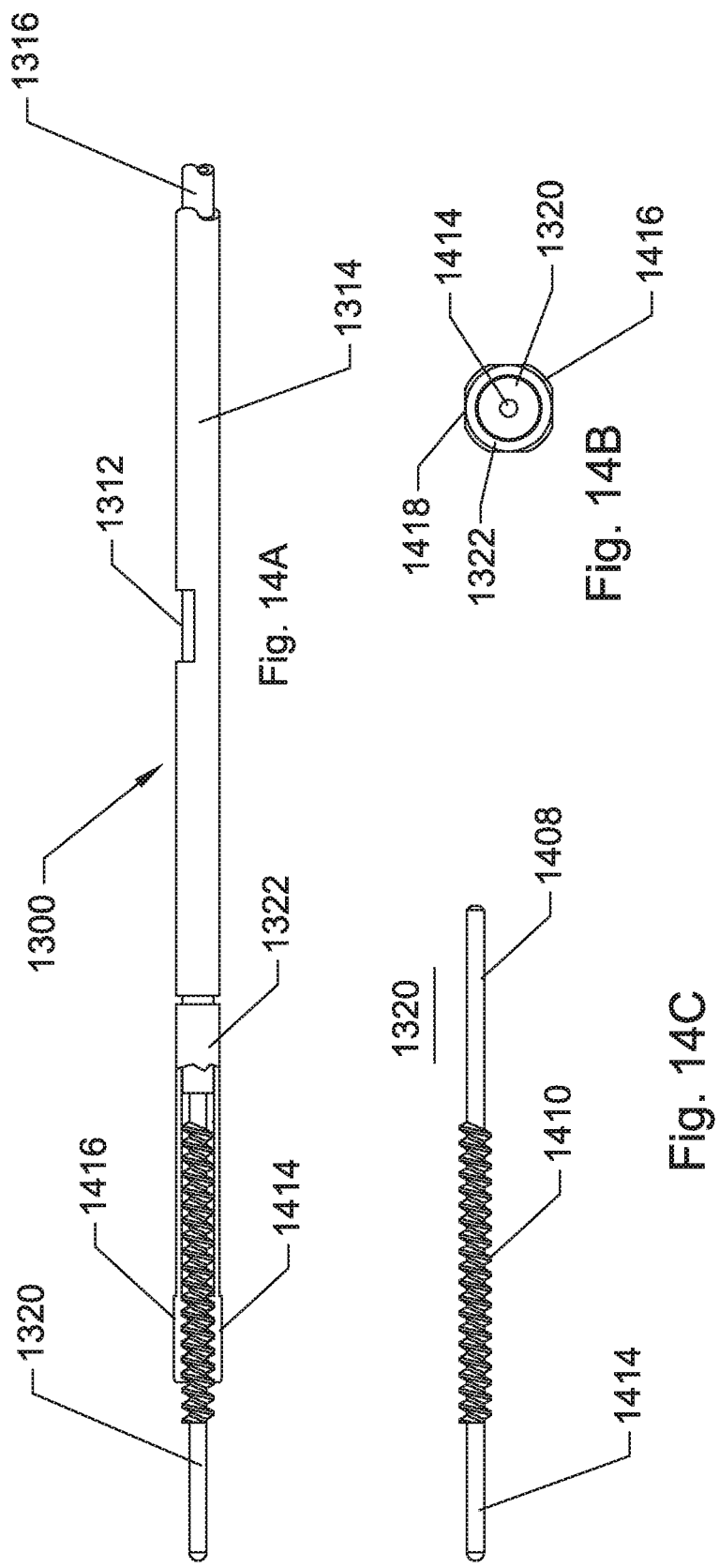

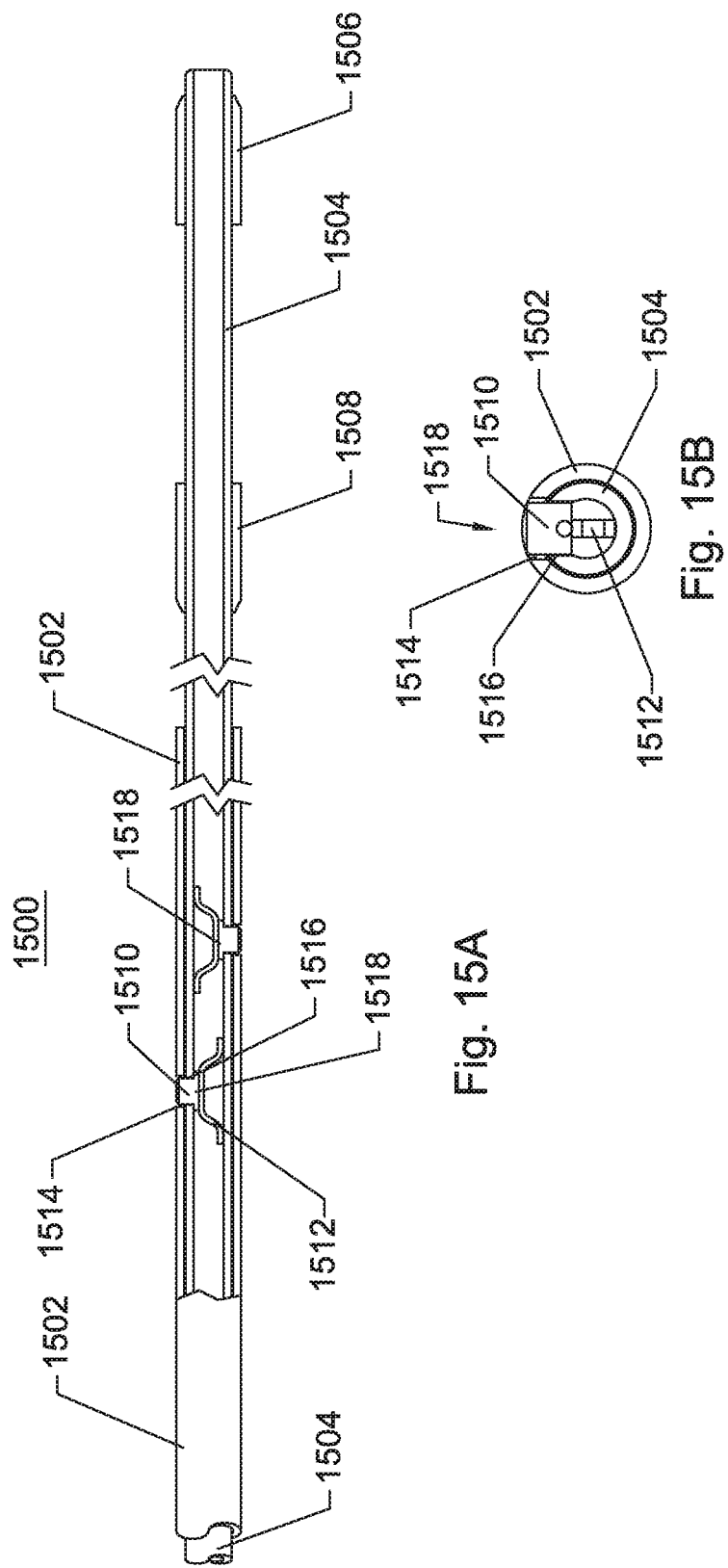

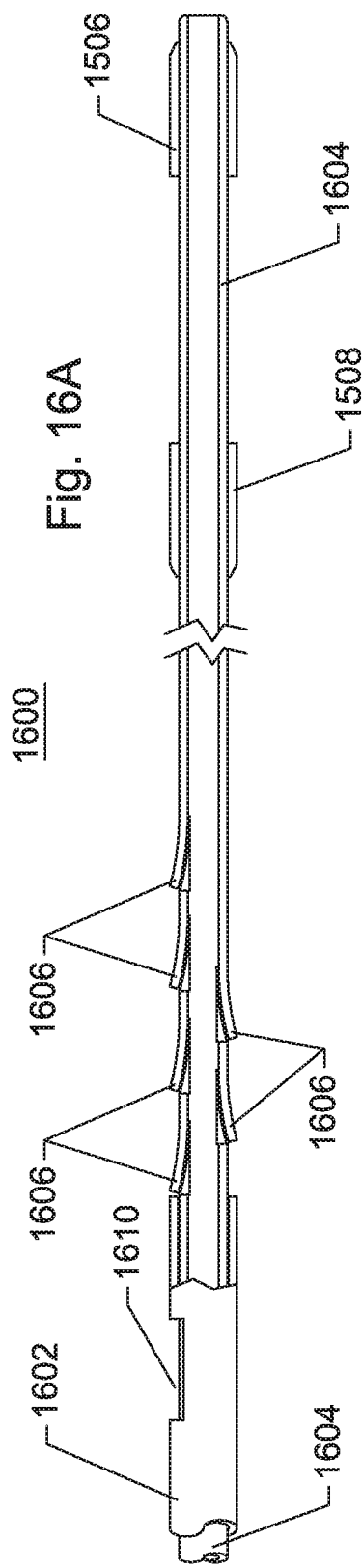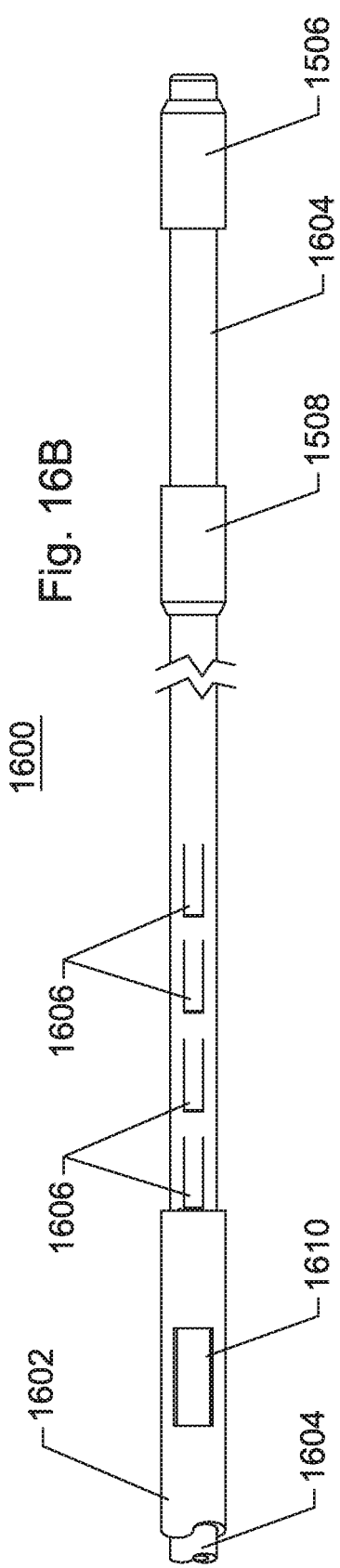

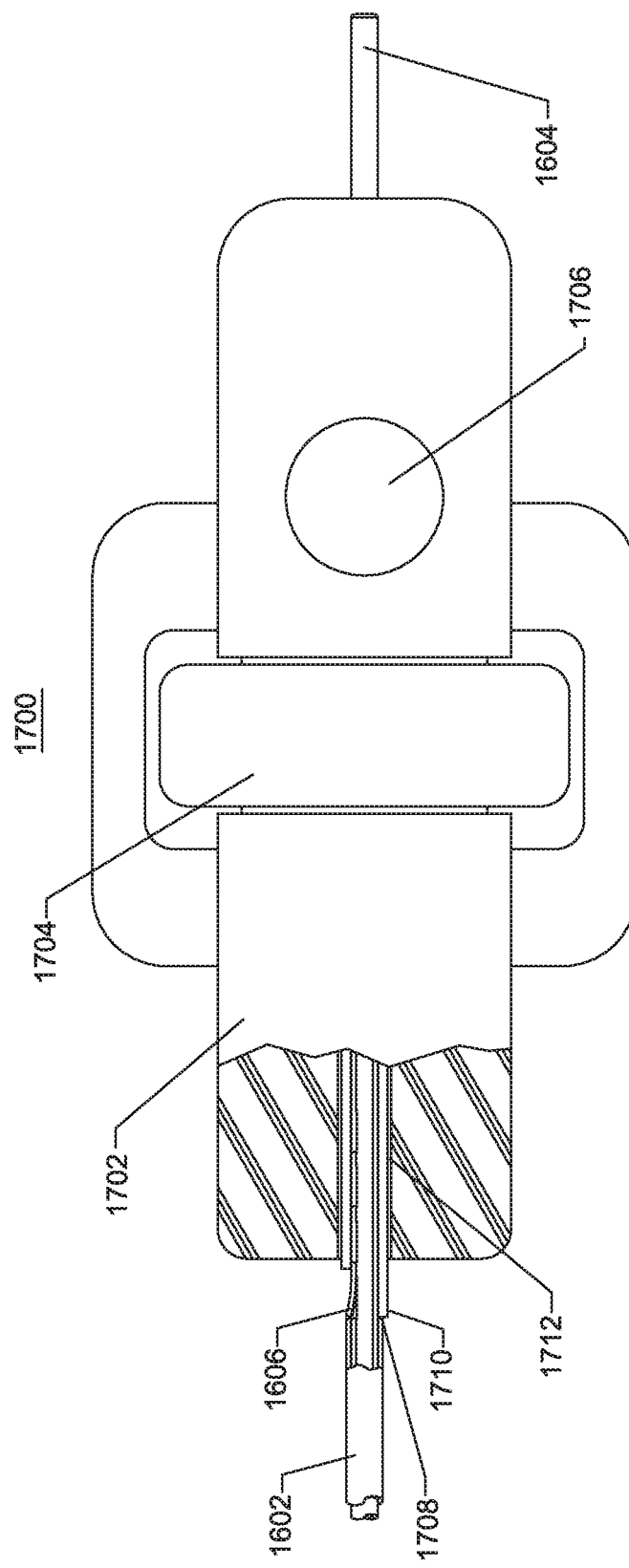

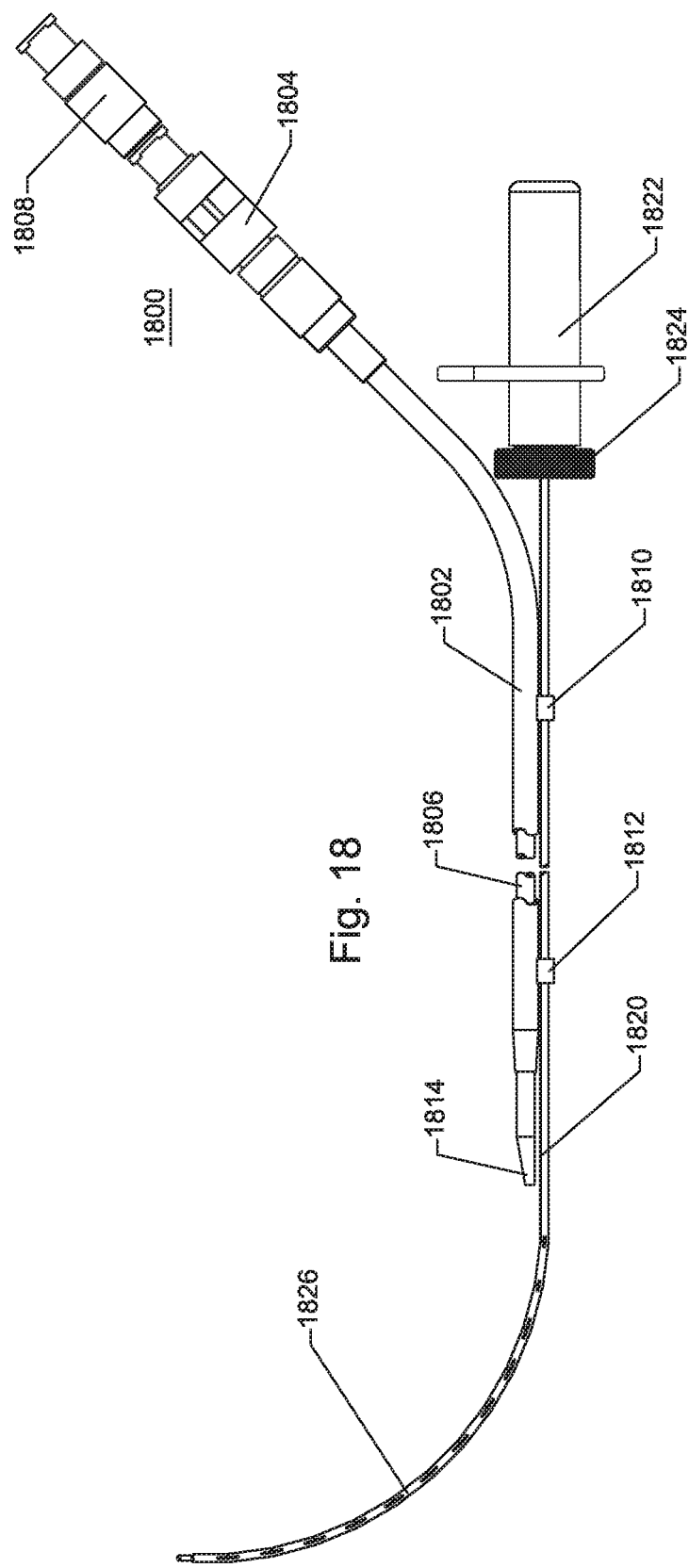

STEERABLE GUIDEWIRE AND METHOD OF USE

This application is a continuation of U.S. application Ser. No. 15/454,924, filed Mar. 9, 2017, now U.S. Pat. No. 10,786,665, which claims priority to U.S. Provisional Application 62/307,691, filed on Mar. 14, 2016 the entirety of which is hereby incorporated by reference.

FIELD OF THE INVENTIONS

The inventions described below relate the field of guidewires.

BACKGROUND OF THE INVENTIONS

During certain interventional procedures that are directed at circulatory access, the patient is catheterized through an access point in a vein or artery. A catheter is routed to the heart or other region of the cardiovascular system through the access point, which may be created by a cutdown or a percutaneous access procedure. The catheter may be routed to a target location within the heart, cerebrovasculature, or other region of the cardiovascular system. The routing is typically performed using a percutaneous access procedure, in some cases called a Seldinger procedure. In other vascular access procedures, open surgical access is required. In either case, a guidewire is advanced into the vasculature by way of the percutaneous or open procedure. The guidewire serves as a tracking system over which a catheter can be routed to a target site within the patient. Guidewires can be used for procedures such as transcatheter, endovascular, or vascular access as well as for transcutaneous, laparoscopic, thoracoscopic, and intramuscular access, and the like.

A pre-bent guidewire can be routed through the vasculature, in conjunction with a guide catheter to permit orienting the distal tip of the guide catheter in the correct direction when a bifurcation or other directional deviation occurs in the vasculature.

SUMMARY OF THE INVENTIONS

A guidewire is disclosed wherein the guidewire is capable of articulating, steering, bending, deflecting, or otherwise being controlled off-axis to permit tracking within a vessel or body tissue, or moving to within a certain target location within a hollow organ. This articulation or steering can be performed without interaction with any guide catheters.

The steerability, deflection, or articulation, of a distal region of the guidewire device can be accomplished using the inner tube and outer tube, concentrically arranged and radially constrained together in the distal region of the guidewire. The inner tube outer diameter is a close tolerance fit to the inside diameter of the outer tube but the inner tube is free to translate along a longitudinal axis of the tubes relative to the outer tube. Thus, only translational motion along the longitudinal axis is used to generate the articulation. The inner tube is modified in a region proximate the distal end such that the inner tube is divided, weakened, or split, into two or more parts along a generally longitudinal direction. Only a portion of these divided parts of the inner tube are affixed, at their proximal end, to the more proximal portion of the inner tube. The parts of the inner tube not affixed at their proximal end can be optionally affixed near their distal end to the portions of the inner tube that are also affixed at their proximal end. The outer tube is rendered flexible by cutting slots or gaps generally having a lateral or radial orientation, although there can be some projection at an angle or along the longitudinal axis of the outer tube. These lateral slots do not pass completely through the outer tubing so a spine with ribs is formed in the outer tubing. The outer tube can be formed as a helix or a coil having a finite spacing between the coils or windings along one or more sides of the distal region. A backbone or series of locking devices can optionally be added to prevent longitudinal compression or expansion on one side of the winding or coil in this configuration. As used herein, the coil construction embodiment having one or more backbones or fixation columns is used interchangeably with embodiments where the distal part of the outer tube which is rendered flexible by way of a plurality of cuts, lateral slots, or the like.

The inner tube can be affixed to the outer tube at a region distal to the lateral slots in the outer tube. The portion of the inner tube that is affixed to the outer tube is that portion of the split inner tube that is connected at its proximal end to the more proximal portions of the inner tube. The inner tube can be configured with a asymmetric distal end, and is preferably split along its length at the distal end. The split is oriented so that it radially migrates toward and through the side of the inner tube on one side. This configuration leaves a connected side or control rod, and a disconnected side or keeper. The disconnected side can be affixed to the connected side near the distal end by a bridge while the connected side is affixed or integral with the inner tube.

A rod with a solid core structure such as a round rod, square rod, C-shaped rod, an X bar, or similar may be used in place of the inner tube.

Thus, articulation is generated using a plurality of (two or more) nested, radially constrained, substantially concentric axially translating tubes, wherein a first tube is weakened on one side to increase flexibility and limit final curvature and shape while a second tube is split substantially longitudinally and broken off on one side within the region where the first tube is also weakened. In certain embodiments, both tubes are substantially in place to maintain hoop strength, column strength, kink resistance, and orientation of discreet structures, such as breaks or slots exist within the plurality of tubes.

The proximal parts of the guidewire can comprise an outer tube that is of standard, unbroken cylindrical configuration with one or more intermediate tubes fabricated from cylindrical tubes of different bendability, cylindrical tubes having flexibility enhancing slots cut therein, closed coils, braided windings, or coils being somewhat open between the windings. The proximal region, the inner tube can be affixed to a solid structure or a wire rather than a tube.

The steerable guidewire can be fabricated to benefit in diameters ranging from about 0.010 inches to about 0.038 inches, or larger. It may be beneficial to build these devices in outside diameters of 0.050 to 0.060 inches or larger. These larger size track devices can be beneficial in larger vessels, such as, but not limited to, the aorta, iliac arteries, superior and inferior vena cava, femoral veins, and the core chambers of the heart such as the ventricles and atria. They can come in various stiffnesses and tip shapes. The guidewire can be made available in undeflected tip configurations such as, but not limited to, a floppy, straight tip, a J-curve tip, and a slight curve tip, for example. The length of a guidewire can range from about 30-cm to about 250-cm or longer. The steerable guidewire can be beneficially, typically twice as long as a catheter which is to be loaded over the guidewire so that the guidewire can remain gripped by the user at both its proximal and distal ends with the catheter fully inserted over the guidewire. A guide catheter can be used in conjunction with the guidewire to achieve some steerability. For example, a guidewire with a curved tip can be withdrawn into a guide catheter to achieve a straight configuration, then be advanced outside the guide catheter into its curve and advanced into a vessel or body lumen, wherein the guide catheter is then advanced along the guidewire until the next steering event is required. The tip curving can be generated by articulation in situ, rather than pre-curving.

The steerable guidewire can be configured with a hub that is permanently attached or it can be configured with a hub that is detachable. The hub can be detachable and re-attachable. The hub may be detachable, re-attachable, and able to provide deflecting control over the distal end, following re-attachment.

The hub can be releasably affixed to the inner and outer tubes using pins, clamps, spring-loaded clamps or pins, or other fasteners. These pins, clamps, and the like can engage the inner tube or rod and outer tube by way of diameter increases, protrusions, bosses, or collars, affixed or integral to the exterior of the tubes or rods. These pins, clamps, and the like can engage the inner tube or rod, the outer tube, or both by way of holes or fenestrations in the tubes. It may be beneficial to be left with a relatively constant outside diameter such that catheters can be routed over the steerable guidewire after the hub and connecting pieces are removed.

The inner tube or rod and the outer tube can have their relative positions maintained after removal of the hub. This maintenance of position can occur by way of one or more pins that engage holes or fenestrations in the inner and outer tube. These pins can be spring loaded in some embodiments. The pins can include round, square, u-shaped, or other cross sectional configurations. The pins can be inserted into the central lumen of the inner tube. They can be routed to a window location in the inner tube and secured at that point from longitudinal or axial movement. When the outer tube window or hole is moved to alignment with the hole or window in the inner tube, the pin can be advanced outward through the hole in the outer tube, thus securing the outer tube and inner tube at a specific longitudinal, and optionally radial, relative position. This methodology can allow for securement at discreet locations consistent with the locations of the holes in the outer tube. A plurality of holes in the outer tube can allow for maintenance of distal curvature at more than one configuration. Selective rotational alignment of the inner tube pin relative to the outer tube can be used to position the inner tube pin at intermediate positions with respect to the outer tube.

The proximal end of the inner tube can comprise an external thread on its exterior. The inner tube is longer than the outer tube such that its proximal end extends out beyond the proximal end of the outer tube. A separate collar with an interior thread can be engaged with the threaded inner tube. The control knob on the hub can be releasably affixed to this threaded collar. Rotation of the threaded collar can exert compression on the proximal end of the outer tube. This compression on the outer tube relative to the inner tube can activate the bending or steering capability of the distal end of the inner tube/control rod and outer tube subassembly. Once the hub with control knob is removed from the inner and outer tube subassembly, the collar can remain in place to precisely maintain the curve at the distal end. This collar is preferentially sized such that its outside diameter is approximately the same or less than that of the outer tube outside diameter. This sizing can permit catheters to be routed over the structure in the manner of a guidewire.

The inner tube can be cut to create a plurality of leaf springs in its surface. Since the inner tube is preferentially a metal with a high modulus of elasticity, e.g. spring temper or spring drawn or rolled, these leaf springs can be configured to bend radially outwardly. These leaf springs can be used to prevent proximal movement of the outer tube relative to the inner tube. Such leaf springs could also be configured to prevent distal movement of the outer tube relative to the inner tube. The outermost radial extent of the leaf springs is preferably not larger than that of the outer tube or the inside diameter of any catheter or dilator that will be threaded over the steerable guidewire. The leaf springs can be compressed radially inward by features on the hub or by separate apparatus. The compressed leaf springs can permit the inner tube and outer tube to slide longitudinally relative to each other. The leaf springs can provide for digital or discreet points of positional locking between the two tubes. The leaf springs can be positioned at various circumferential locations on the inner tube to increase the resolution or difference in locking position between the outer tube and inner tube.

A twist lock can be created at the hub end of the steerable guidewire. Rotation of the twist lock can prevent relative movement of the inner tube relative to the outer tube. This twist lock can take the form of two rectangular or oval tube segments nested within each other. The inner tube is configured with a dimensional increase at its proximal end. By exposing the dimensionally increased part of the inner tube relative to the outer tube and twisting it to approximately 90 degrees from its nested orientation, the inner tube is prevented from moving within the outer tube. This apparatus can provide for one or more discreet locking location. The twist lock can be free to move or it can be spring loaded to control its circumferential position.

The steerable guidewire can be used in the manner of a track over which a catheter can be routed without removal of the hub. Such tracking can take the form of a feature on the side of the catheter that permits longitudinally slidable attachment to the guidewire exterior at points distal to the hub. By way of example, one or more loop structures, c-clips or openable and closable rings, such as carabiners, can be affixed to the side of the catheter. The catheter and, optionally its dilator or obturator, can be routed thus, beside the guidewire and not over it, to a target location in the body to which the guidewire has already been placed. The catheter can beneficially include one or more of these sliding clips and the tip of the catheter can be made asymmetrical such that it tapers toward the guidewire and not to a central point on the cross-section of the catheter and its dilator.

An apparatus adapted for steering a distal end of a guidewire configured for advancement into a mammalian body comprises an inner axially elongate tube having a proximal end, a distal end, and a central lumen within the inner tube that extends substantially the length of the inner tube; an outer axially elongate tube having a proximal end, a distal end, a central lumen within the outer tube that extends substantially the length of the outer tube, where the outer tube comprises a bendable region defined by a plurality of approximately laterally oriented slots extending part way into the outer tube but not completely transecting the outer tube, the inner tube is radially constrained to concentrically reside within the central lumen of the outer tube, and translate along the longitudinal axis of the outer tube, and one or more longitudinal slits in the inner tube divide the inner tube into one or more control rods along its longitudinal axis, the one or more control rods are separated from each other within a region of the laterally oriented slots in the outer tube, and the one or more control rods of the inner tube are affixed to the outer tube distal to the region of the laterally oriented slots in the outer tube. The apparatus further comprises a hub affixed to the proximal end of the inner tube and comprising an internal lumen; and a jack-screw traveler element affixed to the proximal end of the outer tube, where the jack-screw traveler element comprises a traveler thread, the outer tube can move axially relative to the hub and the inner tube in response to movement of the jack-screw traveler element; the internal lumen of the hub is capable of receiving the jack-screw traveler element and preventing the jack-screw traveler element from rotating about the longitudinal axis of the hub, and the inner tube is constrained not to move relative to the hub. The apparatus further comprises a knob affixed to the hub, where the knob is capable of being rotated by a user, and the knob comprises a knob thread such that the knob thread and the jackscrew traveler thread engage.

The inner tube can be a solid rod for at least a portion of its length. longitudinal movement of the outer tube relative to the inner tube causes distortion of the outer tube in a region of the laterally oriented slots and results in selective bending of the outer tube and inner tube in the region of the partially formed laterally oriented slots. In a further embodiment, the longitudinal slit in the inner tube traverses approximately to the proximal end of the outer tube.

The distal end the outer tube can controllably curve between about 0 degrees and at least about 90 degrees from the longitudinal axis of the outer tube. The distal end the outer tube can controllably curve between about 0 degrees and at least about 180 degrees from the longitudinal axis of the outer tube.

Axial tension on the inner tube relative to the outer tube curves a distal end of the apparatus. In a further embodiment attachments of the inner tube to the hub and the outer tube to the jack-screw traveler are reversed such that the inner tube moves relative to the hub and the outer tube is affixed to the hub. The hub may be removable from a proximal end of the apparatus, and when the hub is removed from the proximal end of the apparatus, an outer diameter of the apparatus is approximately the same along a length of the apparatus.

The apparatus may further comprise features preventing axial or longitudinal motion of the inner tube and the outer tube upon removal of the hub. The features preventing axial or longitudinal motion may comprise spring loaded pins that engage openings in a wall of the inner tube or a wall of the outer tube. The features preventing axial or longitudinal motion may comprise leaf springs integral with the inner tube that engage the proximal end of the outer tube. The features preventing axial or longitudinal motion may comprise a small jackscrew affixed to the inner tube and a jackscrew traveler collar that can be rotated by the hub and is able to apply longitudinal forces on the proximal end of the outer tube.

The apparatus further comprise a catheter configured to be routed alongside the guidewire by means of fasteners that open and close around the outer tube. The apparatus may further comprise features that protrude from the inner tube, proximate a proximal end of the apparatus such that the hub can engage the features and lock thereto. The hub may be removable attached to a proximal end of the apparatus. In a yet further embodiment, the apparatus further comprises a removable obturator slidably disposed within the central lumen of the inner tube, where the obturator can be advanced forward out the distal end of the inner tube or it can be removed from the inner tube by withdrawal through the proximal end of the inner tube.

A bendable portion of the outer tube may bends due to off-center forces being exerted on the outer tube by the inner tube. The bendable portion of the outer tube comprises a plurality of approximately laterally oriented slots. The inner tube imparts off-center forces due to a discontinuity in a structure of the inner tube. The hub may be capable of being removed and re-attached to a proximal end of the guidewire, and following re-attachment of the hub, the guidewire deflection at its distal end can be controlled by the re-attached hub. The outer tube may be a composite and comprises coils of wire along at least a portion of its length.

The distal end of the apparatus is blunted and not sharp. The apparatus may further comprise two or more control rods where a first control rod of the two or more control rods is connected to a first jackscrew traveler element and a second control rod of the two or more control rods is connected to a second jackscrew traveler element. The first and second jackscrew traveler elements may be actuated by a single controller. The first and second jackscrew traveler elements may have different thread pitches to accommodate different amounts of linear travel during bending of a distal end of the apparatus. The first and second jackscrew traveler elements may also comprise different hand threads to accommodate travel in different directions during bending of a distal end of the apparatus.

The inner tube may comprise a protrusion near its proximal end and the outer tube comprises a longitudinal slot having one or more cul-de-sacs wherein the protrusion on the inner tube can move longitudinally or axially within the longitudinal slot in the outer tube and rest within the one or more cul-de-sacs such that further longitudinal movement of the inner tube relative to the outer tube is prevented. The inner tube can be rotated slightly at its proximal end relative to the outer tube such that the protrusion can be engaged with and released from engagement of the one or more cul-de-sacs. In a further embodiment, the central lumen of the inner tube is adapted for injection or withdrawal of fluids.

A method of steering a guidewire into a body lumen, tissue, or cavity of mammalian body is disclosed. The method comprises the steps of inserting the guidewire into the body lumen, tissue, or cavity and routing the guidewire to a target site, where the guidewire is substantially straight and uncurved, and the guidewire comprises a bendable region near a distal end of the guidewire and a hub that comprises a control element at a proximal end on the guidewire; deflecting the bendable region near the distal end of the guidewire into a curve, where the deflecting step is performed by application of force by the control element on the proximal end of the guidewire; removing the hub of the guidewire; and advancing a catheter, concentrically over the curved guidewire to the target site by way of a lumen in the catheter or dilator comprised by the catheter.

The deflecting step may further comprise moving a jack-screw traveler within the hub of the guidewire which causes two concentrically nested axially elongate tubes to move longitudinally relative to each other. The deflecting step may further comprise selectively bending an outer tube near the distal end of the guidewire at regions which are selectively more flexible than other regions of the outer tube. The deflection step may further comprise monitoring the step of deflecting the distal end of the guidewire into the curve under MRI, ultrasonic, fluoroscopic or X-ray imaging or visualization. Removal of the hub from the guidewire may results in control forces being removed from the guidewire.

Removal of the hub from the guidewire may result in control forces being maintained within the guidewire such that the curve is approximately maintained. A side of the catheter may be releasably affixed to the guidewire and the catheter is slidably routed beside the guidewire to the target site. The method may further comprise the step of forcing a change in a deflection or curvature of the catheter and obturator by deflection of the bendable region at the distal end of the guidewire. The method may further comprise the step of locking the guidewire such that when the hub is removed, the curve of the guidewire is maintained.

A catheter or other medical instrument can be inserted or routed through a lumen within the inner tube of the guidewire.

BRIEF DESCRIPTION OF THE DRAWINGS

FIG. 1A illustrates a side, partial cutaway view of a steerable guidewire having a hub, a proximal region, an intermediate region, and a steerable distal region.

FIG. 1B illustrates a magnified side, partial breakaway view of a transition between the distal steerable region and the intermediate region of the steerable guidewire of FIG. 1A.

FIG. 2A illustrates a side, partial breakaway, view of an outer tube of a steerable guidewire comprising a plurality of slots near the distal end to generate a region of increased flexibility.

FIG. 2B illustrates a side, partial breakaway, view of an inner, tube of the steerable guidewire comprising a longitudinal slot dividing the tube into two axially oriented parts which are connected at the distal end of the inner tube.

FIG. 7A illustrates a top view of a portion of the distal flexible region of an outer tube comprising dovetails or interlocking grooves to reduce torque or side-to-side motion.

FIG. 7B illustrates a side view of a portion of the distal flexible region of an outer tube comprising dovetails or locking grooves to reduce torque or side-to-side motion.

FIG. 9A illustrates an outer tube cut in its flexible regions with shorter lateral slots and with reduced or complete elimination of some T-slots to improve resistance to bending in that region.

FIG. 9B illustrates an inner tube wherein the disconnected side has been removed, leaving only the connected side and the distal end.

FIG. 14A illustrates a side view, in partial cutaway, of the proximal end of the steerable guidewire of FIG. 13 with the hub removed;

FIG. 14B illustrates a lateral cross sectional view of a jackscrew collar configured to engage the jackscrew and further to apply longitudinal force on an outer tube.

FIG. 14C illustrates the jackscrew element of the steerable guidewire of FIG. 14A.

FIG. 15A illustrates a side, partial cutaway, view of the proximal end of a steerable guidewire which comprises one or more spring loaded pins configured to lock the inner tube to the outer tube at discreet axial or longitudinal locations.

FIG. 15B illustrates a lateral cross-sectional view of the inner and outer tubes of the steerable guidewire of FIG. 15A and further illustrating a spring-loaded pin configuration.

FIG. 16A illustrates a side, partial cutaway view of the proximal end of a steerable guidewire, wherein the inner tube includes cantilever springs integrally formed in its outer structure, the springs configured to engage the proximal end of the outer tube or windows created within the outer tube.

FIG. 16B illustrates a top view of the proximal end of the steerable guidewire of FIG. 16A showing another perspective on the cantilever leaf springs as well as a plurality of locking collars on the inner tube configured to engage with a removable hub.

FIG. 17 illustrates a side view, in partial cross-section, of a hub affixed to a steerable guidewire, wherein the hub comprises a jackscrew to move the inner tube relative to the outer tube, a lock to engage the inner tube, and features to selectively compress springs comprised by the inner tube, and a feature configured to engage the proximal end of the outer tube and move it distally relative to the inner tube. and FIG. 18 illustrates a side view of a side-tracking catheter comprising features to engage the exterior of a steerable guidewire without the need to remove the hub.

DETAILED DESCRIPTION OF THE INVENTIONS

Figure 3:
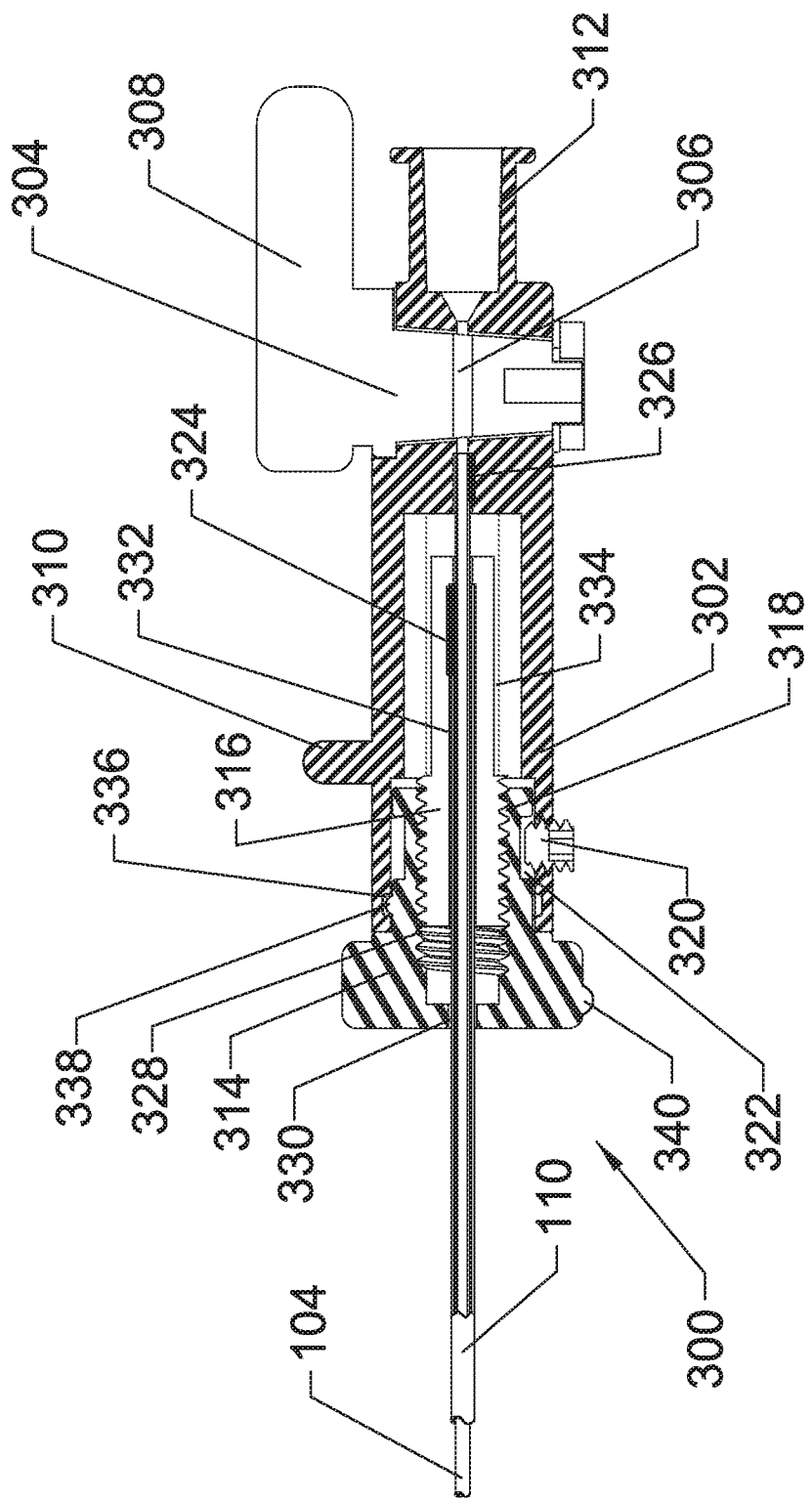
FIG. 3 illustrates a cross-sectional view of the proximal end of the steerable guidewire comprising a stopcock and a bend adjusting mechanism.

The steerable guidewire is an endoluminally, transvascularly, or endovascularly placed steerable guidewire, with internal deflectability or the ability to articulate, at its distal end, in a direction away from its longitudinal axis. The steerable guidewire is generally fabricated from stainless steel, nitinol, or the like and comprises an outer tube, an inner tube, and a distal articulating region. The guidewire can be coated with polymeric coatings such as, but not limited to, fluoropolymers, polyesters, polyamides, and the like. The exterior can further be coated with hydrogels or other materials to facilitate reduced friction, Thromboresistance, antibacterial reactivity, and the like. The deflecting or articulating mechanism is integral to the steerable guidewire. The steerable guidewire is useful for animals, including mammals and human patients and is routed through body lumens or other body structures to reach its target destination.

The steerable guidewire comprises an inner tube and an outer tube. The steerable guidewire can also comprise a stylet or obturator, which can be removable or non-removable. The steerable guidewire further comprises a hub at its proximal end which permits grasping of the steerable guidewire as well as features, or control mechanisms, for controlling the articulation at the distal end. Such features can comprise control knobs, handles, levers, or the like. The proximal end further can optionally be terminated with a female Luer or Luer lock port or hemostasis valve, which is suitable for attachment of pressure monitoring lines, dye injection lines, vacuum lines, a combination thereof, or the like. The steerable guidewire can comprise a center channel operably affixed to the Luer or Luer lock port, said channel being useful for dye injection, material or fluid administration or removal, pressure monitoring, or the like. It may be beneficial that a catheter be advanceable over the guidewire beginning at the proximal end of the guidewire. To accommodate over-the-wire use, the hub, which comprises controlling mechanisms for the distal deflection, is beneficially detachable from the guidewire and can be releasably or non-releasably affixed to the guidewire following advancement of a catheter past the proximal end of the guidewire.

The steerable guidewire is fabricated so that it is substantially straight from its proximal end to its distal end. Manipulation of a control mechanism at the proximal end of the steerable guidewire causes a distal region of the steerable guidewire to bend or curve away from its longitudinal axis. The bending, steering, deflecting, or articulating region is located near the distal end of the steerable guidewire and can be a flexible region or structure placed under tension or compression through control rods or tubular structures routed from the control handle at the proximal end of the steerable guidewire to a point distal to the flexible region.

One method of use involves inserting the central core wire or stylet so that it protrudes out the distal end of the steerable guidewire. A percutaneous or cutdown procedure is performed to gain access to structures such as, but not limited to, the vasculature, either a vein, an artery, a body lumen or duct, a hollow organ, musculature, fascia, cutaneous tissue, the abdominal cavity, the thoracic cavity, and the like. An introducer, which is usually a hollow, large diameter, hypodermic needle, and the steerable guidewire are placed within the vasculature and the steerable guidewire is routed proximate to the target treatment site. The introducer can be removed at this time or substantially at the time the guidewire is introduced into the body lumen. A guiding catheter, preferably with a removable central obturator or dilator having a core lumen sized to slidably fit over the steerable guidewire, with a tapered distal tip pre-inserted, is routed over the steerable guidewire to the target site. The steerable guidewire can be adjusted so that it assumes a substantially straight configuration. The steerable guidewire can be advanced through the central lumen of an already placed catheter, sheath, introducer, or guide catheter. The steerable guidewire comprises a generally atraumatic, non-sharp, distal tip. The distal tip can be rounded, oval, or the like.

The distal end of the steerable guidewire, and optionally the body of the guidewire as well, is sufficiently radiopaque that it is observable clearly under fluoroscopy or X-ray imaging. The steerable guidewire, especially near its distal end, can be configured with asymmetric radiopaque markers that provide some indication regarding the side of the steerable guidewire that deflection can occur. The location of the steerable guidewire and the amount of deflection and curvature of the distal end are observed and controlled using the aforementioned fluoroscopy or X-ray imaging, or other imaging method such as MRI, PET scan, ultrasound imaging, and the like. One or more radiopaque markers can be affixed to the distal end of the steerable guidewire to further enhance visibility under fluoroscopy. Such radiopaque markers can comprise materials such as, but not limited to, thick ferrous metals, tantalum, gold, platinum, platinum iridium, and the like.

Deflection of the distal tip to varying degrees of curvature, under control from the proximal end of the guidewire can be performed. The curve can be oriented along the direction of a branching vessel or vessel curve so that the steerable guidewire can then be advanced into the vessel by way of its high column strength and torqueability. Alignment with any curvature of the catheter can be completed at this time. When correctly positioned under fluoroscopy, ultrasound, or other imaging system, radiopaque dye can be injected into the central lumen of the steerable guidewire at its proximal end and be expelled out of the distal end of the steerable guidewire to provide for road-mapping, etc. This steering function can be very beneficial in device placement and is also especially useful in highly tortuous vessels or body lumens which may further include branching structures such as bifurcations, trifurcations, and the like.

The inner tube, the outer tube, or both can have slots imparted into their walls to impart controlled degrees of flexibility. The slots can be configured as "snake cuts" to form a series of ribs with one or more spines. The spines can be oriented at a given circumferential position on the outer tube, the inner tube, or both. The spines can also have non-constant orientations. In some embodiments, only the outer tube is slotted. The slots can be generated within the distal portion of the outer tube where the curve is generated. This distance can range between about 0.5-cm and 15-cm of the end and preferably between 1-cm and 5-cm of the distal end. The slot widths can range between 0.001 inches and 0.100 inches with a preferable width of 0.002 to 0.010 inches, and more preferably the slot widths are about 0.008 inches. It may be desirable to have the outer tube bend in one direction only but not in the opposite direction and not in either lateral direction. To accommodate this operability, the slots can be made on one side of the outer tubing within, for example, the distal 10-cm of the tube length. Approximately 5 to 30 cuts can be generated with a width of approximately 0.010 to 0.040 inches. The cut depth, across the tube diameter from one side, can range between 0.1 and 0.9 of the tube diameter. Preferably, the cut depth can be approximately 0.4 to 0.6 of the tube diameter with a cut width of 0.025 inches. A second cut can be generated on the opposite side of the tube wherein the second cut is approximately 0.005 inches or less. The outer tube can be bent into an arc first and then have the slots generated such that when the tube is bent back toward the 0.005 inch wide cuts, the tube will have an approximately straight configuration even through each tube segment between the cuts is slightly arced or curved.

FIG. 1A illustrates a side view of a steerable guidewire 100 comprising a distal outer tube 102, an inner control tube or rod 104, an outer low-friction coating 106, an intermediate outer tube 108, a proximal outer tube 110, a hub body 112 further comprising a hub body lumen 124, a jackscrew traveler 114, a control knob 116, a guidewire tip 118, an inner tube lock 120, and a proximal outer tube lock 122.

Referring to FIG. 1A, the distal end of the inner control tube or rod, hereafter called the inner tube, 104 is affixed to the distal end of the distal outer tube 102 with a weld, adhesive bond, fastener, fixation device, or the like. The inner control tube or rod 104 is slidably disposed within the inner lumen of the distal outer tube 102 except at the distal end where they are affixed to each other. The proximal end of the distal outer tube 102 is affixed to the distal end of the intermediate outer tube 108 by a weld, fixation device, adhesive bond, or the like. The proximal end of the intermediate outer tube 108 is affixed to the distal end of the proximal outer tube 110 by a weld, fixation device, adhesive bond, or the like. The entire outer tube assembly 102, 108, 110 can be covered with an optional anti-friction coating or layer 106. The guidewire tip 118 or nose cone is affixed to the inner tube 104, the distal outer tube 102, or both. The guidewire tip 118 can comprise a through hole to permit infusion of fluids therethrough or for advancement of a stylet (not shown) beyond the distal end of the guidewire 100. The control knob 116 is rotationally free to move within the hub body 112, to which it is longitudinally affixed and the two components do not move axially relative to each other. The jackscrew traveler 114 can move axially within a lumen 124 within the hub body 112 within the constraints of the end of the internal lumen 124 of the hub body 112. The jackscrew traveler 114 is keyed within the lumen 124 by a non-round cross-section that impinges on complimentary structures within the lumen 124 to prevent relative rotational movement of the two components 112, 124. The jackscrew traveler 114 comprises external threads that are complimentary and fit within internal threads of the control knob 116. Thus, when the control knob 116 is turned, the jackscrew traveler 114 is forced to move axially either forward or backward because the control knob 116 is longitudinally affixed within the hub body 112.

A thread pitch for the jackscrew traveler 114 and the control knob 116 can range from about 16 to about 64 threads per inch (TPI) with a preferred range of about 24 TPI to about 48 TPI and a more preferred range of about 28 to about 36 TPI.

The hub assembly may be removable from the steerable guidewire so that the proximal end of the steerable guidewire 100 retains the same (or smaller) diameter or profile as the intermediate and distal ends of the guidewire. Catheters, guide catheters, introducers, sheaths, or other axially elongate medical devices comprising an internal guidewire lumen can be slipped over the proximal end of the steerable guidewire and advanced into the patient over an already placed steerable guidewire. This approach provides for catheter exchange, replacement, swapping, or the like. Once the catheter is advanced such that its proximal end is located distal to the proximal end of the steerable guidewire, the hub assembly can be releasably affixed to the proximal end of the steerable guidewire so that the distal end of the guidewire can be deflected under control at the proximal end. The hub assembly illustrated in FIG. 1A provides an outer tube lock 122 and inner tube lock 120 to secure the outer tube 110 and inner tube 104 of the steerable guidewire such that the hub is affixed and in control of the relative axial position of the two tubes. The outer tube lock 122 can be configured as a bayonet mount (as illustrated) or it can comprise a locking button, locking clamp, threaded lock, or the like.

FIG. 1B illustrates a magnified view of the steerable guidewire 100 of FIG. 1A at the transition between the distal end of the intermediate region 108 and the proximal end of the distal, steerable region. The steerable guidewire 100 transition region comprises the intermediate outer tube 108, the distal outer tube 102, the inner tube 104, and the polymeric outer coating 106.

The polymeric outer coating 106 is optional but beneficial and can comprise materials such as, but not limited to, fluoropolymers such as PTFE, PFA, FEP, polyester, polyamide, PEEK, and the like. The polymeric outer coating 106 can render the coiled embodiment of the intermediate outer tube 108, as illustrated, to retain a relatively smooth exterior surface and provide for friction reduction which is useful when passing a long, slender guidewire through a long, catheter lumen. The distal outer tube 102 can be affixed to the intermediate outer tube 108 by means of a weld, fastener, adhesive bond, embedment with polymeric, metallic, or ceramic materials, or the like. The intermediate outer tube 108, illustrated in this embodiment as a coil structure with substantially no spacing between the coils, is highly flexible and the flexibility can be controlled by the elastic modulus, thickness, and other material properties of the outer coating 106. The intermediate outer tube 108, in other embodiments, can comprise structures such as, but not limited to, an unperforated or unfenestrated tube, a tube with partial lateral cuts, a spiral cut tube, a ribcage with a backbone, or the like.

FIG. 2A illustrates a side view, in partial breakaway, of the distal end of the axially elongate distal outer tube 102, comprising a lumen 214, a proximal, uncut portion 212, a plurality of lateral partial cuts 216, and a plurality of longitudinal "T" cuts 218. The distal outer tube 102 serves as the outer tube of the steerable guidewire such as that illustrated in FIG. 1. The plurality of partial lateral cuts 216 serve to render the region of the outer tube 102 in which the lateral cuts 216 are located more flexible than the proximal region 212. The plurality of longitudinal "T" cuts, serve to further render the region of the outer tube 102, in which the "T" cuts 218 reside, more flexible than in tubes where such "T" cuts 218 were not present. The longitudinal "T" cuts 218 are optional but are beneficial in increasing the flexibility of the outer tube 102 in the selected bend region. The partial lateral slots 216 can be spaced apart by about 0.02 to about 1.0 inches with a preferred range of about 0.1 inches to about 0.8 inches and a further preferred range of about 0.15 inches to about 0.5 inches. In an exemplary embodiment, the partial lateral slots 216 are spaced about 0.17 inches apart. The spacing between the partial lateral slots 216 can vary. The spacing between the partial lateral slots toward the proximal end of the outer tube 102 can be about 0.3 inches while those partial lateral slots 216 nearer the distal end of the outer tube 102 can be spaced about 0.15 inches apart. The spacing can change in a step function, it can change gradually moving from one end of the outer tube 102 to the other, or it can increase and decrease one or more times to generate certain specific flexibility characteristics. Increased spacing increases the minimum radius of curvature achievable by compression of the partial lateral slots 216 while decreased spacing allows for a smaller minimum radius of curvature.

The number of lateral cuts 216 or, optionally, the number of lateral cuts 216 with T-cuts 218 can number between about four and about 50 with a preferred number being between about six and about 25 and a more preferred number of about eight to about fifteen. In the illustrated embodiment, there are 12 partial lateral cuts 216, each modified with a "T" slot 218. In other embodiments, the partial lateral cuts 216 can be shaped differently. For example, the partial lateral cuts 216 can be at angles other than 90 degrees to the longitudinal axis, curved, V-shaped, Z-shaped, W-shaped or the like. In other embodiments, the 'T' slots 218 can have, for example, further cuts approximately lateral to the longitudinal axis, along any portion of the "T" cut 218.

The outer tube 102 can have an outer diameter of about 0.010 to about 0.1 inches with a preferred outside diameter of about 0.015 to about 0.050 inches and a more preferred diameter of about 0.020 inches to about 0.035 inches. In the illustrated embodiment, the outside diameter is about 0.048 inches while the inner diameter is about 0.036 inches. The inside diameter of the outer tube 102 can range from about 0.0.005 inches to about 0.090 inches.

FIG. 2B is a side view, in partial breakaway, of the distal end of an axially elongate inner tube 104, comprising a lumen 224, a proximal, uncut portion 222, a longitudinal slot 226 further comprising an angled lead in 228, a free side 234, a pusher or connected side 232, and a distal tip 230. The distal tip 230 interconnects the free side 234 and the pusher side 232. The distal tip 230 or end of the inner tube 104 can further comprise a rounded, tapered, or blunted tip or nose cone (not shown). The disconnected free side 234 and the connected pusher side 232 are generally integrally formed but can also be affixed to each other by welding, adhesives, fasteners, or the like.

The lead in 228 to the longitudinal slot 226 is beneficially angled to prevent other guidewires, stylets, or other devices, which are inserted through the central lumen 224 from being caught or bumping against an edge. The angled lead in 228 serves a guide to assist with traverse of a stylet, obturator, or guidewire past the lead in 228 and into the distal region of the steerable guidewire. The lead in 228 can be angled from between about −80 degrees (the angle can be retrograde) from the longitudinal axis (fully lateral) to about +2 degrees and preferably from about +5 degrees to about +20 degrees with a most preferred angle of about +8 degrees and about +15 degrees. In the illustrated embodiment, the angle of the lead in slot 228 is about 10 degrees from the longitudinal axis. A second feature of the lead in 228 is that it be positioned or located proximally to the most proximal "T" slot 218 in the outer tube 102 when the two tubes 102, 104 are affixed to each other (see FIG. 9). The lead in 228 is located at least 1-cm proximal to the proximal most "T" slot 218 and preferably at least 2-cm proximal to the proximal most "T" slot 218 so that bending in the distal region does not distort the lead in 228 and cause kinking, misalignment, or pinching of the internal lumen 224.

The inner tube 104 can have an outside diameter that is slightly smaller than the inside diameter of the outer tube 102 so that the inner tube 104 can be constrained to move longitudinally or axially within the outer tube 102 in a smooth fashion with relatively little force exerted. In the illustrated embodiment, the outside diameter of the inner tube 104 is about 0.033 inches giving about a 0.0015 inch radial clearance between the two tubes 102 and 104. The inside diameter of the inner tube 104 can range from about 0.006 to about 0.015 inches less than the outside diameter of the inner tube 104. In the illustrated embodiment, the wall thickness of the inner tube is about 0.006 inches so the inside diameter of the inner tube is about 0.021 inches. The lumen 224 of the inner tube 104 can be sized to slidably accept a stylet or obturator 140 such as illustrated in FIGS. 1 and 2. A typical stylet wire 140 can range in diameter from about 0.01 to about 0.23 inches with a preferred diameter range of about 0.012 to about 0.020 inches. The outer tube 102 may have an outside diameter of about 0.050 inches and an inside diameter of about 0.038 inches. In this embodiment, the inner tube 104 has an outside diameter of about 0.036 inches and an inside diameter of about 0.023 inches. The radial wall clearance between the inner tube 102 and the outer tube 104 is about 0.001 inches and the diametric clearance is about 0.002 inches. The annulus between the two tubes must be substantially smooth, free from burrs, and free from contamination because the two tubes 102, 104 beneficially need to translate along their longitudinal axis relative to each other over relatively long axial distances of about 50 to about 150-cm.

The inner tube 104 transmits force along its proximal non-slotted region 222 from the proximal end of the inner tube 104 to the lead in 228 where the force continues to be propagated along the connected side 232 to the distal end 230. The outer tube 102 transmits force along its proximal non-slotted region 212. Longitudinal forces applied to the distal, flexible region with the slots 216 cause deformation of the outer tube in an asymmetrical fashion with the side of the outer tube 102 comprising the partial lateral slots 216 forming an outer curve if the slots 216 are expanded and an inside curve if the slots 216 are compressed. Forces to cause bending are preferably exerted such that the partial lateral slots 216 are compressed up to the point where the gap closes, but no further, however forces can also be exerted to expand the slots 216, however limits on curvature are not in place because the lateral slots 216 can open in an unrestrained fashion except for the material properties of the outer tube 102.

The disconnected side 234 of the inner tube 104, separated from the connected side 232 by the longitudinal slot 226 and the lead in 228, serves to maintain an undistorted tube geometry and provide resistance to deformation while helping to maintain the inner lumen 224 in a round configuration and provide a shoehorn or funnel effect to guide an obturator, guidewire, or stylet 140 therethrough as they are advanced distally. The disconnected side 234, being separated from the force transmitting member 222 cannot provide any substantial longitudinal load bearing structure, although at its distal end, where it can be integral or affixed to the distal end 230, some tension load carrying capability exists. The inner tube 104 can be considered a split tube and does not carry a load in compression or tension along substantially the entire length of the disconnected side 234. A main advantage of keeping the disconnected side 234 is to maintain the off-center positioning of the force transmitting member 222. The disconnected side 234 can be termed a keeper or stay since it merely serves to fill the space between the connected side 232, or control rod, and the outer tube wall.

The partial lateral slot 216 in the inner tube 104 and the T-Slot 218 in the outer tube 102, as well as the longitudinal slot 226 in the inner 104, and the lead in slot 228 can be fabricated by methods such as, but not limited to, electron discharge machining (EDM), wire EDM, photo chemical etching, etching, laser cutting, conventional milling, or the like. In other embodiments, different slot configurations can also be employed, such as curved slots, complex slots, zig-zag slots, or the like. The partial lateral slot 216 can be configured with a tongue and groove or dovetail design to prevent or minimize lateral movement or torqueing of the outer tube 102 in the flexible region. The tongue and groove or dovetail (not shown) can be generally centered between two "T" slots, for example. The parts can be ganged and fixture such that, using wire EDM, for example, a plurality of tubes can be cut to reduce manufacturing costs. As many as 20 to 30 tubes, or more, can be fixtured, secured, and etched by the aforementioned methods.

FIG. 3 illustrates a side, cross-sectional view the hub end 300 of a steerable guidewire. The hub end 300 comprises the outer proximal tube 110, the inner tube 104, a hub body 302, a stopcock petcock 304 further comprising a petcock handle 308 and a petcock through bore 306, a Luer lock fitting 312, a keyed lumen 334, a setscrew or pin 320, a jackscrew body 316 further comprising a plurality of threads 328 and a central lumen 332, a control knob 314 further comprising a plurality of threads 318, a central lumen 330, the protrusion 338, and a circumferential recess 322, an outer tube weld 324, an orientation mark 340, and an inner tube weld 326. The hub body 302 can further comprise a plurality of recesses or complementary structures 336. The hub 300 can also comprise an arrow pointer 310 to assist in orientation of the direction of curvature at the distal end of the steerable guidewire by reference points on the hub 300.

Referring to FIG. 3, the petcock 304 is affixed to the petcock handle 308 by welding, integral fabrication, fasteners, adhesives, or the like. The petcock 304 is retained within a lateral through bore in the hub body 302, which is in the illustrated embodiment, tapered, using a locking "C" washer, fastener, screw, pin, or the like (not shown). The petcock 304 can be rotated about its longitudinal axis to align the through bore 306 with the axis and central lumen of the hub body 302 or it can be rotated sideways to shut off and seal the lumen against the flow of fluids. The Luer lock 312 can be affixed to, or integrally fabricated with, the hub body 302. The knob 314 is retained within the hub body 302 by the setscrew of pin 320 which prevents axial movement but permits rotational movement as constrained by the setscrew, projection, or pin 320 riding within the circumferential recess 322 which is integrally formed or affixed to the knob 314. The jackscrew body 316 is capable of axial movement within the hub body 302 but is restrained from rotation about the long axis by flats or features on the exterior of the jackscrew body 316 which are constrained by flats or features in the keyed lumen 334. The knob 314 comprises threads 328 on its internal lumen which engage with external threads 318 on the jackscrew body 316. Rotation of the knob 314 thus causes the jackscrew body 316 to move axially proximally or distally with mechanical advantage. Rotation of the knob 314 can be forced using manual action or using a motor or other mechanism (not shown). The proximal outer tube 110 can be affixed to the jackscrew body 816 by the outer tube weld 824. The inner tube 104 (which can also be called the intermediate tube) is affixed to the hub body 302 by the inner tube weld 326. The central lumen 224 of the inner tube 104 is operably connected to a central lumen of the hub body 302, the petcock through bore 306, and the lumen of the Luer fitting 312.

The knob 314 can comprise markings 340 to permit the user to visualize its rotary or circumferential position with respect to the hub body 302. These markings 340 can comprise structures such as, but not limited to, printed alphanumeric characters (not shown), a plurality of geometric shapes such as dots, squares, or the like, or the markings can comprise raised or depressed (embossed) characters of similar configuration as described for the printed markings. The knob 314 can comprise a number on each of the facets so the facets can be numbered from one to 6, in the illustrated embodiment. The knob markings 340 can further comprise raised structures, as illustrated, which can further be enhanced with contrasting colors for easy visualization. The number of facets can range from about three to about 50.

The knob 314 can further comprise one or more complementary structures affixed or integral thereto, such as a plurality of protrusions 338 that fit into detents 336 affixed or integral to the proximal end of the hub body 302. Such protrusions extending into detents in the hub body 302 can provide a ratcheting or clicking sound as well as providing resistance to inadvertent movement of the knob 314 once it is rotated to the correct location. The knob 314, in some embodiments, can be biased toward the hub body 302 to ensure that complementary structures such as the protrusions and detents come into correct contact. In other embodiments, the knob 314 can comprise a ratchet system to further control its rotary movement with respect to the hub body 302. In other embodiments, the knob 314 can comprise one or more detents (not shown) while the hub body 302 can comprise one or more complementary protrusions (not shown). It is beneficial that the knob 314 be moved only when required by the user and not by accident or not when it is required to maintain its rotary position and, by consequence, the curvature at the distal end of the tubing. The number of ratchet locations, or low energy positions or set points, can range from about 2 per 360 degree rotation to about 20 with a preferred number of ratchet locations ranging from about 4 to about 12.

The hub body 302 can be fabricated from biocompatible metals such as, but not limited to, stainless steel, titanium, nickel coated brass, cobalt nickel alloy, and the like, although it could also be fabricated from polymeric materials in a less expensive format. The knob 314 can be fabricated from the same metals as the hub body 302 but it can beneficially be fabricated from biocompatible polymers such as, but not limited to, polyamide, polyimide, polyvinyl chloride (PVC), acrylonitrile butadiene styrene (ABS), acetal polymers, polycarbonate, polysulfone, PEEK, Hytrel®, Pebax®, and the like. The petcock 304 and petcock handle 308 can be fabricated from the same materials as the knob 314, or it can be different materials. The jackscrew body (or traveler) 316 can be fabricated from the same materials as the hub body 302, or from different materials, but must be able to be strongly affixed to the outer tube 102.

The arrow pointer 310 can be affixed to the hub body 302 or other component. The arrow pointer 310 is used to indicate the direction of bending or deflection at the distal end of the steerable guidewire by reference points on the hub but due to torsional effects on such a long device as a guidewire, the primary guide for orientation will be the fluoroscopic or X-Ray images taken of the distal end of the steerable guidewire, in vivo. The hub system 300 illustrated in FIG. 3 is not detachable or releasable from the proximal end tubes 110 and 104. In other embodiments such as that of FIG. 1, the hub system 300 can be made to slide onto the tubes 110, 104 and clamp by means of locking mechanisms. In yet other embodiments, the hub 300 can be made to split open along its axis and then re-close and latch over the proximal ends of the tubes 110, 104.

Figure 4:
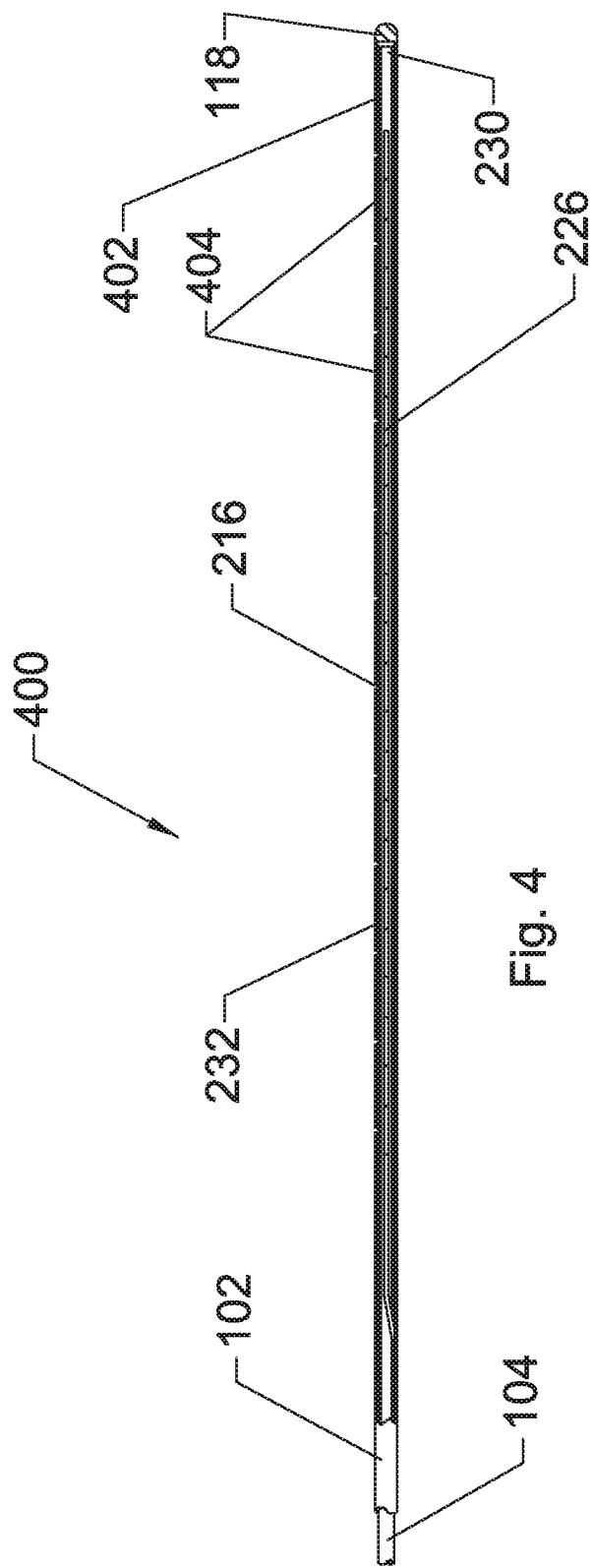
FIG. 4 illustrates a partial breakaway view of the distal end of the steerable guidewire comprising the outer tube and the inner tube arranged concentrically and oriented circumferentially.

FIG. 4 illustrates a side view, in partial breakaway, the distal end 400 of a steerable guidewire. The distal end 400 comprises the distal outer tubing 102 further comprising the lateral partial slits 216 and the intermediate (or inner) tubing 104 further comprising the longitudinal slit 226 and the distal inner tube tip 230. A weld 402 affixes the distal end of the outer tubing 102 to the connected side 232 of the intermediate tubing. The distal end 400 can further comprise one or more separate radiopaque markers 404 and a nose cone or distal fairing 118, which may or may not comprise a central lumen. The distal outer tube 102 and the inner tubing 104 are rotated about the longitudinal axis such that the connected side 232 of the inner tube 104 is generally aligned with, and affixed or welded 402 to, the distal outer tubing 102 on the side comprising the partial lateral slits 216. The width of the partial lateral slits 216, the T-slots 218, and the longitudinal slot 226 can range from about 0.001 to about 0.050 inches with a preferred range of about 0.005 to about 0.020 inches. In the illustrated embodiment, the slits 216, 218, and 226 are about 0.010 inches. The width of the partial lateral slits 216 on the outer tube 102 can be used, in compression to provide at least some limit to how much the distal outer tube 102 can bend in compression along the side comprising the partial lateral slits 216. Note that the inner tube 104 extends beyond the distal end of the distal outer tube 102. In the illustrated embodiment, the inner tube 104 extends about 10 mm to about 20 mm beyond the distal end of the distal outer tube 102. This construction provides for reduced device complexity, increased reliability of operation, and reduced manufacturing costs relative to other steerable devices. The steerable guidewire, in the embodiments presented herein, has high column strength, and resistance to torque.

The distal end 400 of the steerable guidewire can be generally fabricated from metals with sufficient radiopacity or radio-denseness that they are clearly visible under fluoroscopic or X-ray imaging. However, if this is not the case, additional radiopaque markers 404 can be affixed to the outer tube 102, the inner tube 104, or both. These radiopaque markers 404 can comprise materials such as, but not limited to, tantalum, gold, platinum, platinum iridium, barium or bismuth compounds, or the like. The radiopaque markers 404 can be beneficially oriented in an asymmetrical manner, as illustrated, to denote the direction of bending to an observer viewing an X-ray image of the distal end 400.

Close tolerances between the internal diameter of the outer tube 102 and the outside diameter of the inner tube 104, ranging from a radial gap of between about 0.0005 inches to about 0.008 inches, depending on diameter cause the two tubes 102 and 104 to work together to remain substantially round in cross-section and not be ovalized, bent, kinked, or otherwise deformed. This is especially important in the flexible distal region comprising the partial lateral cuts 216 on the distal outer tube 102 and the longitudinal slot 226 in the inner or inner tube 104. The two tubes 102 and 104 can be fabricated from the same materials or the materials can be different for each tube 102, 104. Materials suitable for tube fabrication include, but are not limited to, stainless steel, nitinol, cobalt nickel alloy, titanium, and the like. Certain very stiff polymers may also be suitable for fabricating the tubes 102, 104 including, but not limited to, polyester, polyimide, polyamide, polyether ether ketone (PEEK), and the like. The relationship between the inner tube 104, the distal outer tube 102, and the slots 216, 218, 226, 228 serve to allow flexibility and shaping in high modulus materials such as those listed above, which are not normally suitable for flexibility. The internal and external surface finishes on these tubes 102, 104 are preferably polished or very smooth to reduce sliding friction between the two tubes 102, 104 because of their very small cross-sections and their relatively long lengths. Lubricants such as, but not limited to, silicone oil, hydrophilic hydrogels, hydrophilic polyurethane materials, PFA, FEP, or polytetrafluoroethylene (PTFE) coatings can be applied to the inner diameter of the distal outer tube 102, the outer diameter of the inner tube 104, or both, to decrease sliding friction to facilitate longitudinal relative travel between the two tubes which is necessary for articulating the flexible, slotted region near the distal end 400 of the articulating, deflectable, or steerable guidewire. The exterior surface of the distal outer tube 102 can be covered with a polymeric layer, either substantially elastomeric or not, which can cover the slots 216, 218, etc. and present a smoother exterior surface to the environment as well as optionally maintaining a closed fluid path through the lumen of the guidewire. The exterior surface can be affixed or configured to slip or slide over the exterior of the outer tube 102.

The weld 402 affixes the distal outer tube 102 to the intermediate or inner tube 104 such that they cannot move relative to each other along the longitudinal axis at that point. However, since the two tubes 102, 104 are affixed to each other on the side of the distal outer tube 102 containing the partial lateral slots or gaps 216, compression or expansion of those gaps 216 can be accomplished by moving the weld 402 by relative movement of the inner tube 104 and the outer tube 102. The weld transmits the force being carried by the connected side 232 of the inner tube 104 to the slotted side of the distal outer tube 102. The inner tube 104 may be an intermediate tube 104 if another tube, wire, stylet, or catheter is passed through its internal lumen 224.

In other embodiments, since the inner tube 104 is split 226 lengthwise in the flexible region, a portion, or the entirety, of the distal end of the inner tube 104 can be affixed, adhered, welded, fastened, or otherwise attached to the distal outer tube 102 and functionality can be retained. The distal end 230 of the inner tube 104 can, in some embodiments be retained so as to create a cylindrical distal region 230 in the inner tube 104 and this entire cylindrical distal region 230, or a portion thereof that does not project distally of the distal end of the outer tube 102 can be welded to the outer tube 102 around a portion, or the entirety of the circumference of the outer tube 102. If only a portion of the inner tube 104 is welded to the distal outer tube 102, then the weld is beneficially located, approximately centered, on the side of the distal outer tube 102 comprising the partial lateral slots 216. The cylindrical distal region 230 is a beneficial construction, rather than completely cutting the inner tube 104 away on one side, since the distal region 230 projects distally of the distal end of the distal outer tube 102 to form the tip of the steerable guidewire further comprising a nose cone or distal fairing 118. The distal nose cone or fairing 118 can be affixed to the distal outer tube 102, the distal end 230 of the inner tube 104, or both, using methodology such as, but not limited to, fasteners, welds, adhesive bonding, and the like.

In some embodiments, one of the welds, all of the welds, or a portion of the welds can be completed using techniques such as, but not limited to, TIG welding, laser welding, silver soldering, fasteners, adhesives, plasma welding, resistance welding, interlocking members, or a combination thereof. Laser welding is beneficial because it is highly focused and can be located with high accuracy. These welds include the weld 402 at the distal end that connects the inner tube 104 and the distal outer tube 102 as well as the welds at the proximal end connecting the inner tube 104 to the hub and the distal outer tube 102 to the traveler of the jack-screw 316.

Figure 5:
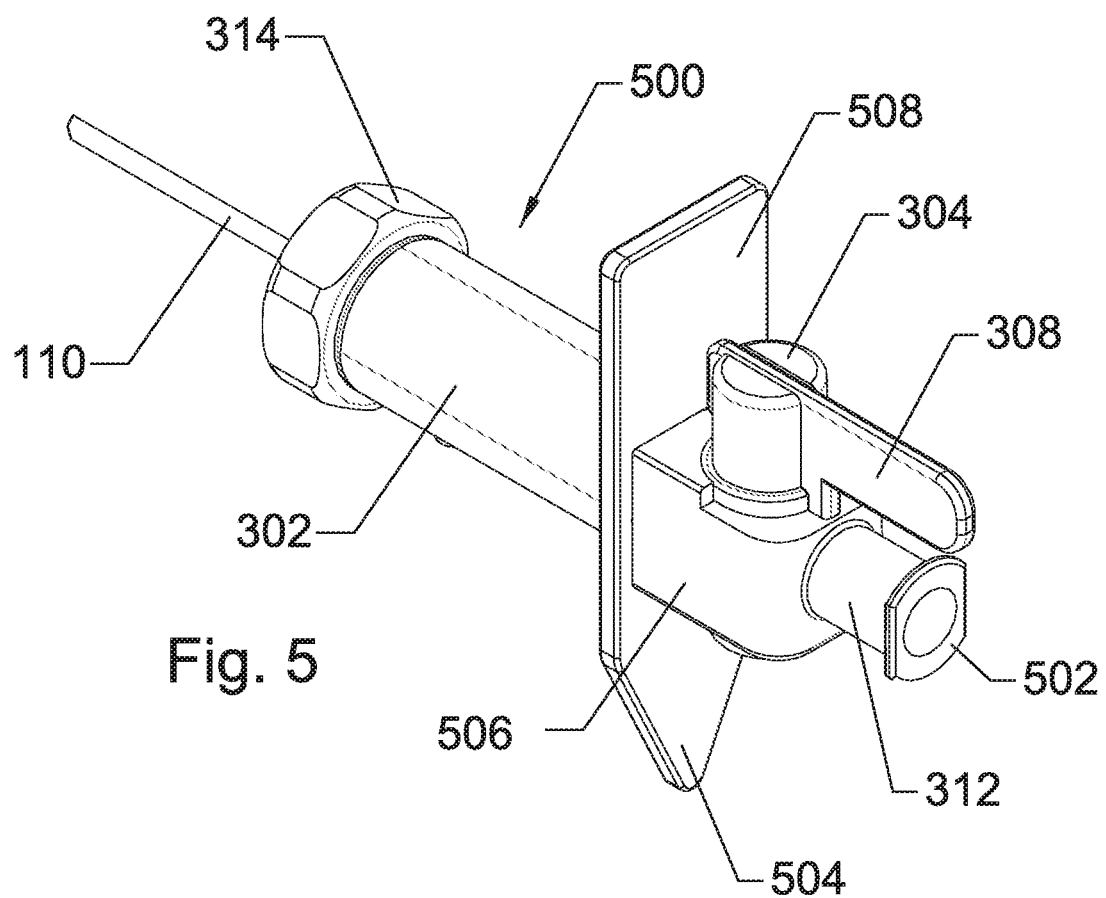
FIG. 5 illustrates an oblique view of the proximal end of the steerable guidewire.

FIG. 5 illustrates an oblique external view of the proximal end 500 of the steerable guidewire comprising the outer tube 110, the knob 314, the hub body 302, the arrow pointer 508 further comprising the pointed end 504, a stopcock body 506, the petcock 304, the petcock handle 308, and the Luer fitting 312 further comprising a locking flange 502. In this embodiment, the hub can be configured to be removable or it can be configured to be permanently affixed to the proximal end of the outer proximal tubing 110 and the inner tubing 104 (not shown).

Referring to FIG. 5, the pointed end 504 of the arrow pointer 508 can be integrally formed with the arrow pointer 508, or it can be affixed thereto. The arrow pointer 508, which is optional, can be integrally formed with the hub body 302, or it can be affixed thereto using fasteners, welds, adhesives, brazing, soldering, or the like. The stopcock body 506 can be integrally formed with the hub body 302 or it can be affixed thereto using fasteners, welding, soldering, brazing, adhesives, threads, bayonet mounts, or the like. Referring to FIGS. 3 and 5, the lumen of the Luer fitting 512 is operably connected to the through bore of the petcock 304 if the petcock 304 is aligned therewith (as illustrated), or the petcock 304 can be rotated about an axis to misalign the through bore of the petcock 304 with the Luer fitting 512 and prevent fluid flow or passage of solid material therethrough. The knob 314 can be round, shaped as a lever, it can comprise knurls, facets (as illustrated), or it can comprise a plurality of projections which facilitate grabbing and rotation by the user. Circumferential motion of the knob 314 about is longitudinal axis is preferably and beneficially smooth but with sufficient friction to maintain its position in any desired configuration.

Figure 6:
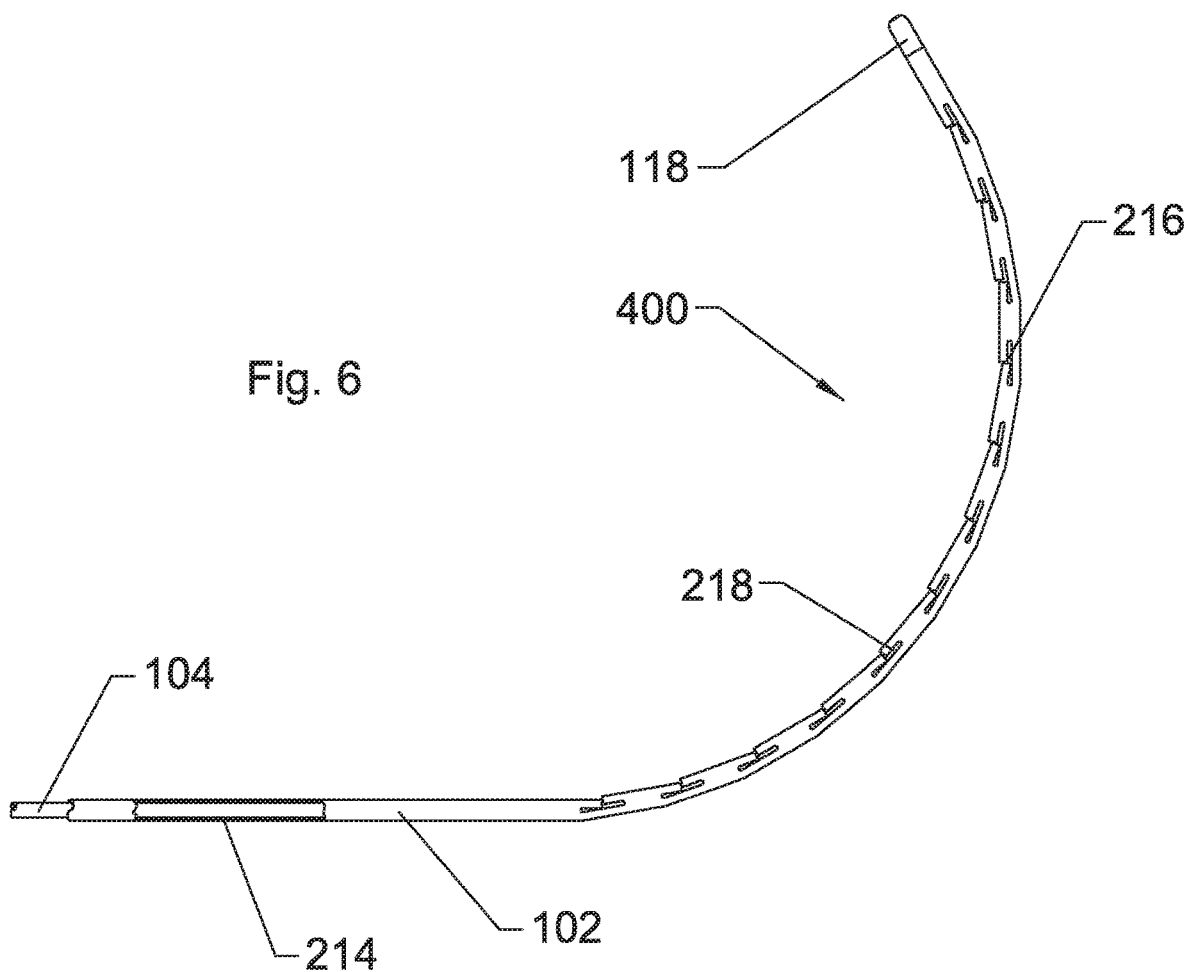
FIG. 6 illustrates a side view of the distal end of the steerable guidewire incorporating the inner split tube and the outer T-slotted tube with the inner tube being pulled proximally relative to the outer tube causing the outer tube to deform into a curve.

FIG. 6 illustrates the distal end 400 of the steerable guidewire in a curved configuration. The distal end 400 comprises the distal outer tube 102, the inner tube 104, the outer tube lumen 214, the nose cone 118, the plurality of outer tube longitudinal cuts or slots 218, and the plurality of outer tube partial lateral cuts 216.

Referring to FIG. 6, the outer tube partial lateral cuts 216 represent spaces that close up when the side of the tube in which the lateral cuts 216 are located is placed in compression. Such compression is generated by pushing the outer tube 102 distally relative to the inner tube 104. When the partial lateral cuts 216 gaps close, further compression is much more difficult because the outer tube 102 stiffens substantially when no further gap exists for compression. The composite structure, with the inner tube 104 nested concentrically inside the outer tube 102 is relatively stiff and resistant to kinking no matter what amount of curvature is being generated.

Preferred radius of curvatures for the distal end can range from about 0.25 inch to about 6 inches, with a preferred range of about 0.5 inches to about 2 inches and a more preferred range of about 0.5 to about 1.5 inches. The radius of curvature need not be constant. The proximal end of the flexible region can have the partial lateral cuts 216 spaced more widely than those at the distal end of the flexible region, causing the distal end to bend into a tighter radius than, the proximal end of the flexible region. In other embodiments, the distal region can be less flexible than the proximal end of the flexible region.

The partial lateral cuts 216, and the "T"-slots in the outer tube 102 are beneficially treated using etching, electropolishing, passivation, sanding, deburring, machining, or other process to round the external edges of the partial lateral cuts 216. Thus, the edges are blunted or rounded so they are not sharp such as to cause the steerable guidewire to dig, skive, or shave material from the inside of a catheter, dilator, or obturator.

FIG. 7A illustrates a top view of another embodiment of an outer tube 700 in the region of the distal, flexible section, wherein the outer tube 700 comprises a plurality of partial lateral cuts or slots 706 further comprising a dovetail 702. The dovetail 702 creates a groove 702 and further comprises a peg or projection 704 that rides or is circumferentially constrained within the groove 702 as long as the outer tube 700 is neutrally forced, or forced in compression on the side of the partial lateral cuts or slots 706. The projection 704 riding within the dovetail groove 702 provides for torque resistance and torsional rigidity in the area of the dovetail 702.

FIG. 12B illustrates a side view of the outer tube 700 in the region of the distal, flexible section, wherein the outer tube 700 comprises the partial lateral slots 706, the dovetail 702 further comprising the projection 704, and the "T" slots 218. The T-slots 218 are optional or they can be configured differently.

The steerable guidewire can be used in the cardiovascular system, the pulmonary system, the gastrointestinal system, or any other system comprising tubular lumens, where minimally invasive access is beneficial. The steerable guidewire of the present invention is integral and steerable. It is configured to be used with other catheters that may or may not be steerable, but the steerable guidewire disclosed herein does not require external steerable catheters or catheters with steerability to be steerable as it is steerable or articulating on its own. The steerable guidewire is capable of bending and unbending a practically unlimited number of times. The steerable guidewire is especially useful with catheters that are not steerable since the steerable guidewire comprises its own steering system.

The steerable guidewire can be removed from the lumen of a catheter following completion of its task. Without removal of the steerable guidewire, the lumen is compromised and the capacity of the sheath to introduce catheters is reduced, given a certain outside diameter. This device is intended for use with catheters and is not intended for use as integral to a catheter. The steerable guidewire device steers itself and can steer a catheter but is not a replacement for a steerable catheter.

The steering mechanism disclosed herein can be used to steer other types of catheters, guide catheters, introducers, sheaths, guidewires, punches, needles, or even obturators that are placed within the aforementioned devices, with high degree of control over long lengths up to 250 cm or more while requiring less wall thickness and thus allowing for larger internal lumens than steerable devices of the prior art with the same outside diameter. Typical sheaths can have internal lumens with capacities of, for example, 3-Fr to 12-Fr and still maintain very thin walls of around 1-Fr. While smaller catheters or guide catheters with lumens in the range of about 2-Fr to 5-Fr can have even smaller wall thicknesses, depending on the materials used to construct the walls of the sheath. Some sheath constructions can comprise composite materials such as an inner tube fabricated from metal and an outer tube fabricated from metal with a polymeric exterior coating. The inner tube can further be coated with an interior liner of, for example PTFE, or other fluoropolymers (PFA, FEP), Parylene, Pebax®, Hytrel®, polyimide, polyamide, PET, or the like, to create certain reduced frictional properties, electrically insulating properties, or both. These coatings or liners can range in thickness from about 0.0001 to about 0.005 inches, with a preferred thickness range of about 0.0005 to 0.002 inches.

The steering mechanism disclosed herein, comprising two or more nested axially elongate cylindrical tubes moving relative to each other only along the longitudinal axis, can provide a high degree of precision, repeatability, force, column strength, torsional control, and the like, in a configuration with extremely thin walls and large inside diameter (ID) to outside diameter (OD) ratio. One of the tubes comprises partial lateral cuts or complex lateral gaps and the other tube comprising a split running substantially the length of the flexible region. The disconnected side of the slit tube can be removed so that only a partially formed, connected side remains. However, in preferred embodiments, the disconnected side, which is actually retained at the distal end, is not removed but serves to fill space within the lumen of the outer tube 102 to prevent kinking, improve column strength, prevent lumen collapse and provide for guiding of central stylets or catheters. Prior art devices require greater wall thickness, which reduces the size of the internal lumen relative to a given outside diameter, or they do not have the same degree of precise movement at the distal tip under control from the proximal end of the device.

Figure 8:
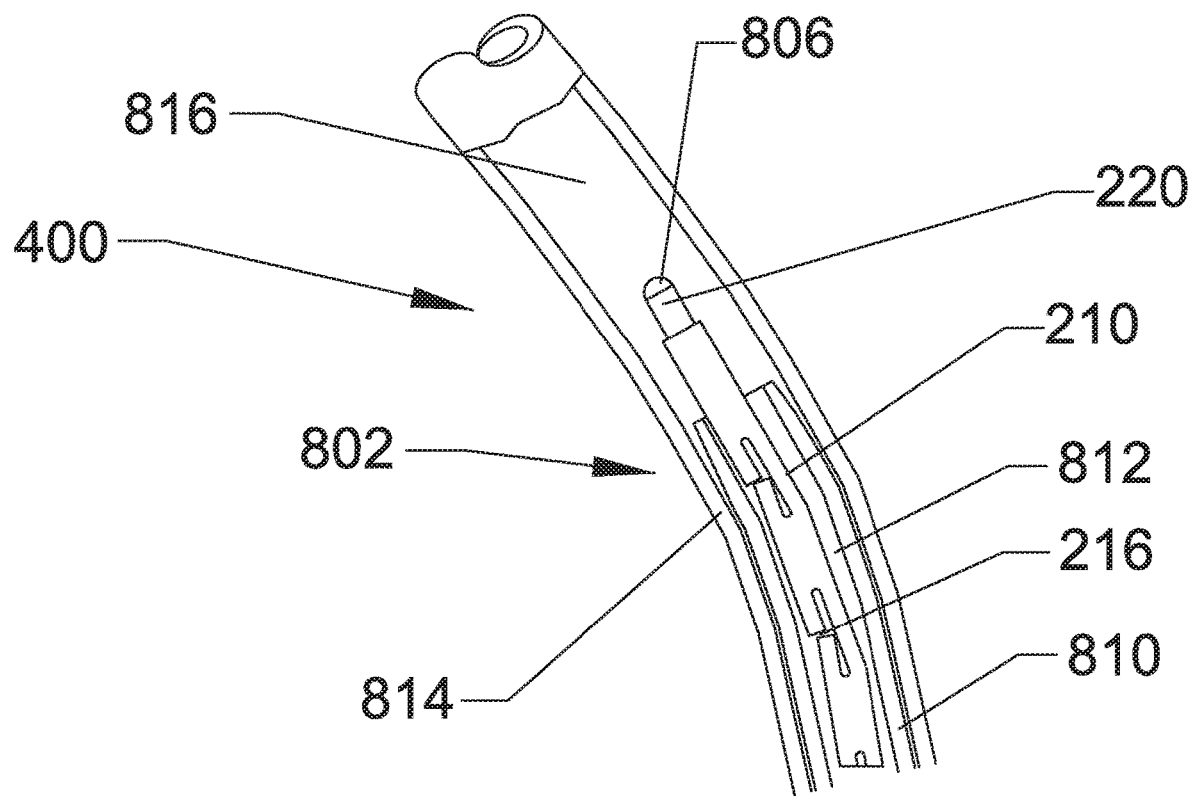
FIG. 8 illustrates the distal end of a steerable guidewire advanced nearly to the distal end of an obturator or dilator, which is coaxially, removably assembled into the central lumen of a guide catheter sheath.

FIG. 8 illustrates a side view of the distal end 400 the steerable guidewire advanced through a central lumen 812 of a dilator or obturator 810 of a guide catheter 814. The steerable guidewire distal end 400 comprises the outer tube 102, comprising the plurality of partial lateral cuts 216, and the inner tube 104, comprising a distal end 220. The distal end 220 comprises, or is terminated by a rounded, blunted, atraumatic distal end 806. The steerable guidewire 400 can further comprises a central lumen (not shown). The guide catheter 814 further comprises a central lumen 816.

The outer tube 102 can be modified to adjust stiffness. It can be preferential to increase the resistance to bending moving distally to proximally on the outer tube 102. This increase in bending resistance contravenes the tendency of the outer tube to bend more severely at the proximal end of the flexible region than in the distal region. It is possible to configure the bending so that the bend radius is approximately constant or such that a greater curvature (smaller radius of bending) is generated moving toward the distal end of the bendable region. The partial lateral slots 216 can be cut with reduced depth more proximally to increase the resistance to bending imparted by the outer tube 102. The partial lateral slots 216 can be cut more narrowly in the more proximal regions to reduce the distance the slot 216 can close. The T-slots 218 can be reduced in length or removed in the more proximal regions of the flexible region of the outer tube 102. Elastomeric bumpers or fillers can be added to some of the partial lateral slots 216 to reduce the amount the partial lateral slots 216 can compress. Once the partial lateral slots 216, associated with the T-slots 218 have closed under bending of the outer tube 102, further bending is resisted and is substantially arrested. By tailoring the width and spacing of the partial lateral slots 216, a specific final curvature can be tailored for a given catheter.

FIG. 9A illustrates the outer tube 102 comprising the lumen 214, the proximal tube wall 212, the plurality of partial lateral slots 216, the plurality of T-slots 218, a short partial lateral slot 902, a slightly longer partial lateral slot 904, and a standard length lateral slot 216 but with a shortened T-slot 906.

Referring to FIG. 9A, the most proximal partial lateral slot 902 penetrates less than the standard partial lateral slots 216. The second (moving distally) partial lateral slot 904 is slightly longer than slot 902 and therefore is more flexible in that region and requires less force to generate bending. The third partial lateral slot comprises the shortened T-slot 906 which reduces the ability of the tubing to bend given a constant bending force.

FIG. 9B illustrates the inner tube 104 comprising the lumen 224, the proximal region 222, the connected side 232, the distal end 230, the rounded tip 118, and a beveled lead-in 910 at the proximal end of the distal end 230.

Referring to FIG. 9B, the proximal end of the disconnected region can be moved distally to increase the stiffness of the inner tube 104 in a specific region, generally the most proximal part of this distal, flexible region.

In certain preferred embodiments, it is beneficial that the inner tube 104 can sustain compression to generate bending of the outer tube 102 at the distal end back to straight after being curved and even to bend beyond straight in the other (or opposite) direction. In order to sustain compression, it is beneficial that the disconnected side 234 be separated from the connected side 232 at or near substantially the center or midpoint of the tubing. Depending on the width of the slot 226 separating the disconnected side 234 from the connected side 232, the location of the slot can be offset from the midpoint but this is dependent on the wall thickness of the inner tube 104 and the angle of the slotting. In a preferred embodiment, interference exists between the disconnected side 234 and the connected side 232 such that the disconnected side and force transmitting member cannot move substantially inward, a situation that would have negative effects of obstructing the lumen, restricting fluid flow therethrough, trapping stylets or other catheters that need to move longitudinally therein, or buckling sufficiently to prevent application of longitudinal compression forces on the connected side 232.

Figure 10A:
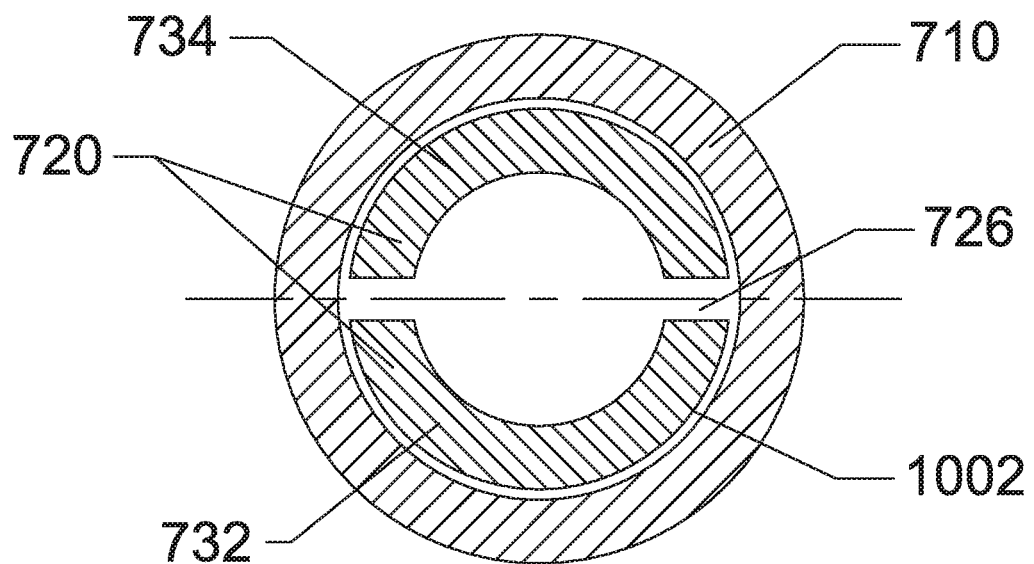
FIG. 10A illustrates a cross-sectional view of a tubing configuration in a steerable guidewire within the flexible region, wherein the separation slot in the inner tube is substantially at the midpoint or center of the inner tubing.

FIG. 10A illustrates a lateral cross-sectional view an inner tube 104 nested inside an outer tube 102 and separated from the outer tube 104 by a radial gap 1002 in the flexible region of a steerable guidewire wherein the inner tube 104 is separated by a split or gap 226 into two approximately or substantially equal parts, a connected side 232 and a disconnected side 234, approximately (or substantially) at the midline or centerline of the cross-section.

Figure 10B:
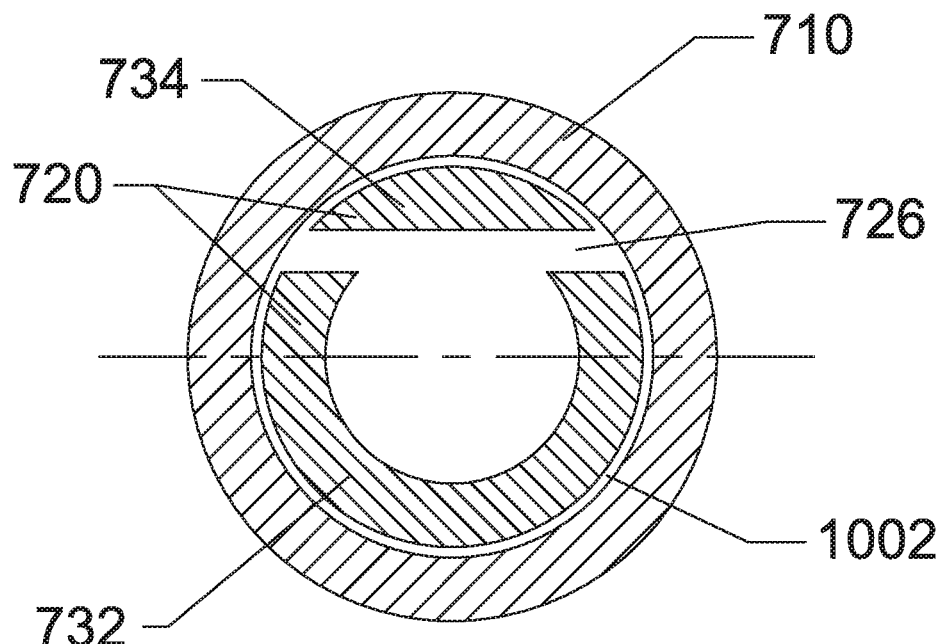
FIG. 10B illustrates a lateral cross-section of a tubing configuration of a steerable guidewire within the flexible distal region, with an off-center slot.

FIG. 10B illustrates a lateral cross-sectional view an inner tube 104 nested inside an outer tube 102 and separated from the outer tube 104 by a radial gap 1002 in the flexible region of a steerable guidewire wherein the inner tube 104 is separated by a split or gap 226 into two substantially unequal parts, a connected side 232 and a disconnected side 234, substantially offset from the midline or centerline of the cross-section.

Referring to FIGS. 10A and 10B, the disconnected side 234 is retained in close proximity to the outer tube 102 by its stiffness and its inability to deform such that the edges of the disconnected side 234 can pass beyond the edges of the connected side 232 and thus the two sides 232 and 234 are retained radially displaced from centerline. If the gap 226 were too large or either side 232, 234 were small enough to fit within the edges of the other side, then displacement of one side toward the centerline and confounding of the off-center orientation of the connected side 232 or 234 would occur leading to buckling of the connected side 232 in compression and inability to straighten out a bent steerable guidewire. Another problem might be loss of torqueability and predictability of the direction of bending. Both embodiments shown in FIGS. 16A and 16B maintain circumferential and radial orientation of the inner tube connected side 232 relative to the disconnected side 234 and promote high precision deflection of the distal tip.

In preferred embodiments, the radial gap 1002 is minimized and is retained between about 0.0005 to 0.002 inches when the steerable guidewire is about 0.035 inches in outside diameter. Furthermore, the split or gap 226 should be as minimal as possible and in preferred embodiments can range from about 0.0005 inches to about 0.003 inches with a gap of about 0.0005 to 0.02 inches being most preferable.

Figure 11:
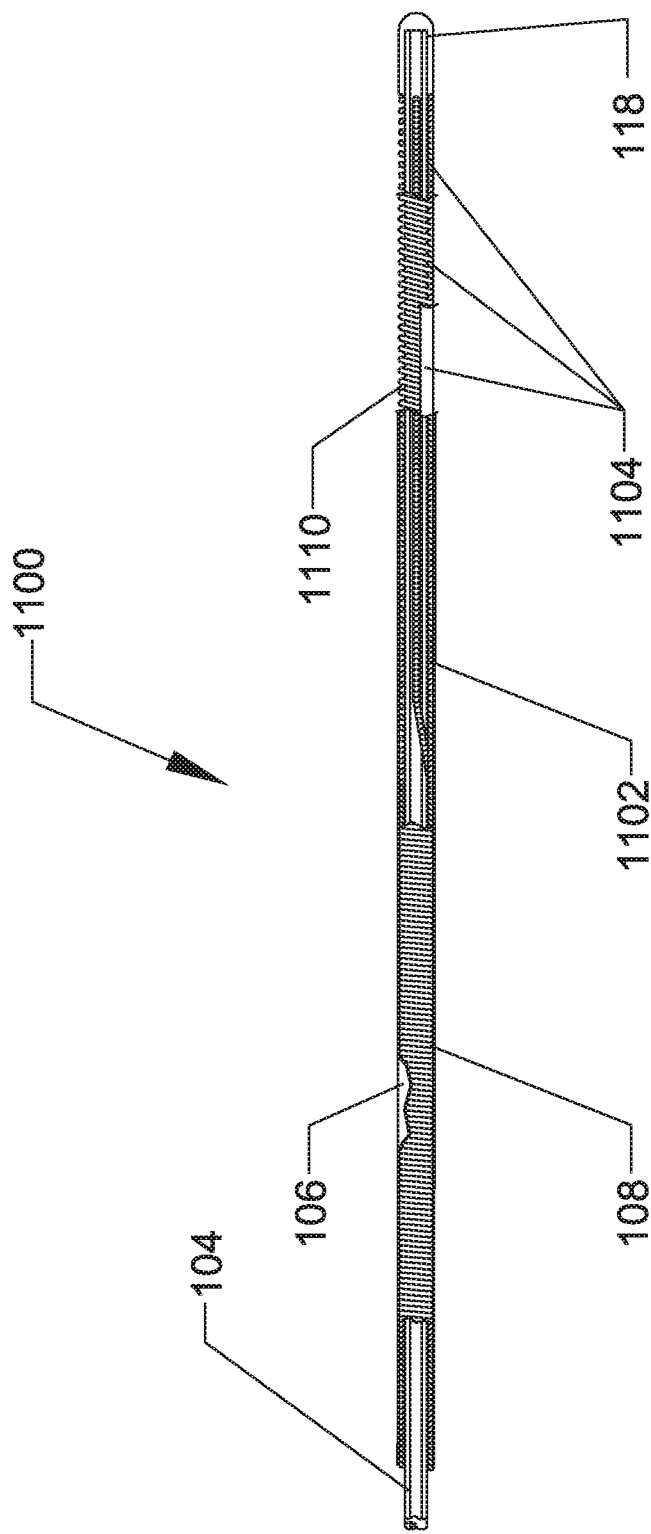
FIG. 11 illustrates a side, partial cutaway view of the distal end of a steerable guidewire wherein the outer tube comprises a coil or helix with a small amount of space between the windings.

FIG. 11 illustrates a side, partial breakaway view of the distal end of a steerable guidewire 1100 as well as a portion of the intermediate region. The steerable guidewire 1100 comprises the inner tube 104, the coiled intermediate outer tube 108, the distal outer coil 1102, the nose cone 118, the backbone 1104, the polymeric outer coating 106, and the distal coil spaces 1110.

The polymeric outer coating 106 can extend the entire length of the steerable guidewire 1100 (or 100) or it can extend only over a portion of the length and can correspond to certain sections such as the proximal section, one or more intermediate section 108, the distal region 1102, or a combination thereof. The polymeric outer region can comprise an elastomer such as, but not limited to, Hytrel, Pebax, polyurethane, silicone rubber, or the like, and can be coated with an additional anti-friction coating such as silicone oil, silicone grease or gel, fluoropolymer, polyimide, or the like.

The distal coil 1102 is affixed, at its proximal end, to the distal end of the intermediate coil 108 and at its distal end to the nose cone 118. The inner tube 104 is affixed to the distal coil 1102 in a region proximate the nose cone 118 such that most or nearly all the distal coil is controlled in expansion and contraction by the inner tube 104. The distal coil 1102 comprises the spaces 1110 which can range in magnitude from 0.0005 inches to about 0.020 inches or greater. In the illustrated embodiment, the coil spaces 1110 are about equal in width to the coil element diameter. The coil element diameters can range from about 0.0005 inches to about 0.010 inches and preferentially ranges from about 0.001 inches to about 0.007 inches in diameter. The coil materials can comprise materials such as, but not limited to, nitinol, polyimide, stainless steel, titanium, cobalt nickel alloy, or the like. The coil materials beneficially comprise material properties of low malleability and high spring hardness.

Referring to FIGS. 11 and 2, the backbone 1104 is located on the side 234 of the steerable guidewire 1100 where the inner tube 104 is disconnected from more proximal structures. Thus, axially oriented forces transmitted through the connected side 232 cause the spring coil 1102 to compress or expand longitudinally with more freedom and less restriction on the connected side 232, as imposed by the backbone 1104, than on the disconnected side 234. This results in an asymmetric force loading on the distal end and causes the distal end to deflect away from the longitudinal axis under control from the proximal end of the steerable guidewire 1100.

Figure 12:
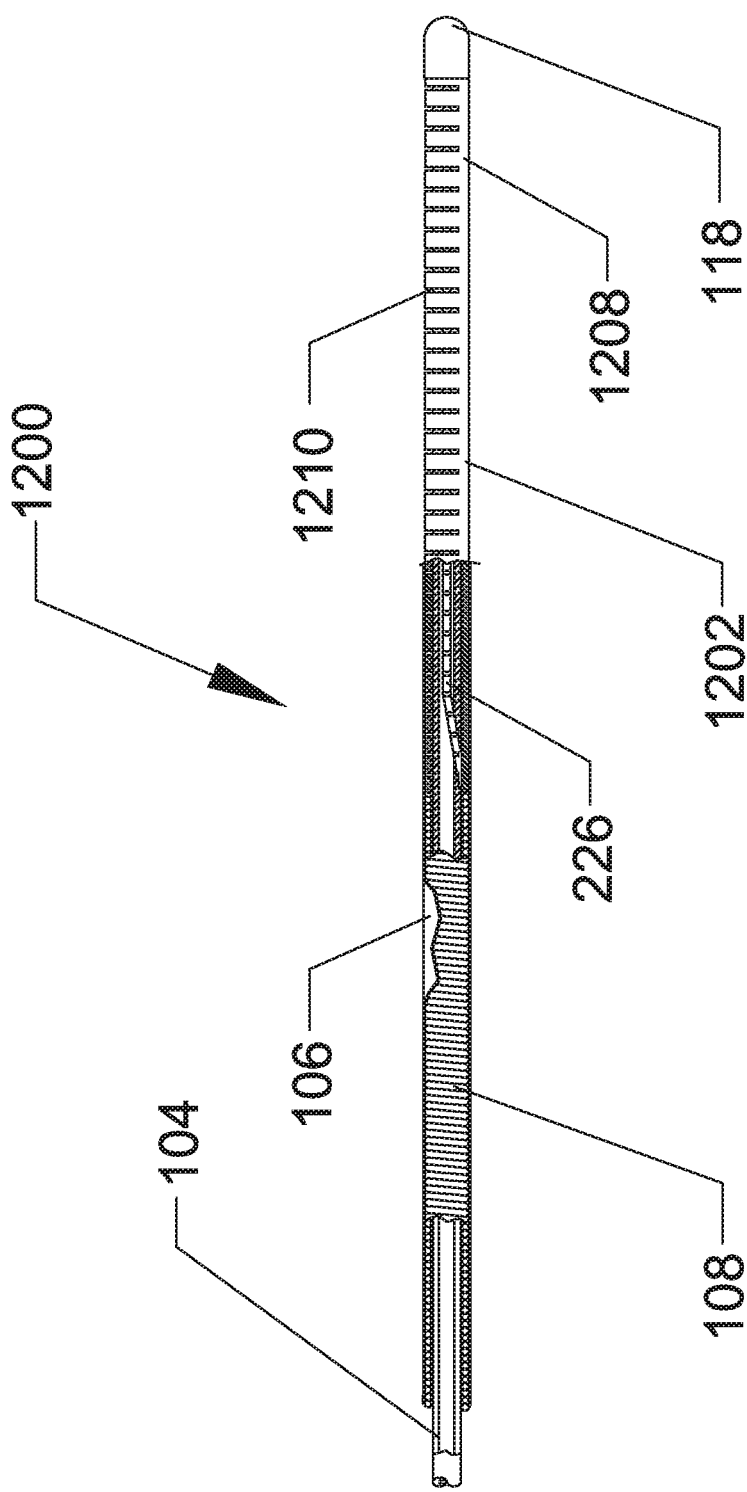
FIG. 12 illustrates a side, partial cutaway view of the distal end of a steerable guidewire wherein the outer tube comprises a cut tube having a backbone and ribs.

FIG. 12 illustrates the distal end of a steerable guidewire 1200 comprising the inner tube 104 further comprising the longitudinal slot 226, the intermediate outer tube 108, the polymeric covering 106, the nose cone 118, a distal outer tube 1202 further comprising a plurality of lateral gaps 1210 and a backbone 1208.

Referring to FIG. 12, the distal outer tube 1202 can be fabricated as a tube comprising the slots 1210 or gaps that are imparted by way of EDM, wire EDM, laser cutting, photochemical etching, conventional machining, or the like. The proximal end of the distal outer tube 1202 is affixed to the distal end of the intermediate outer tube 108. The distal end of the distal outer tube 1202 is affixed to the tip or nose cone 118. The distal end of the outer tube 1202 is also affixed to the inner tube 104 substantially distal to the distal end of the longitudinal slot 226 to prevent rotational and lateral relative movement at that point. The backbone 1208 forces asymmetric lengthening and compression of the gaps 1210 thus generating a lateral bend or curve out of the longitudinal axis in the distal outer tube 1202.

Figure 13:
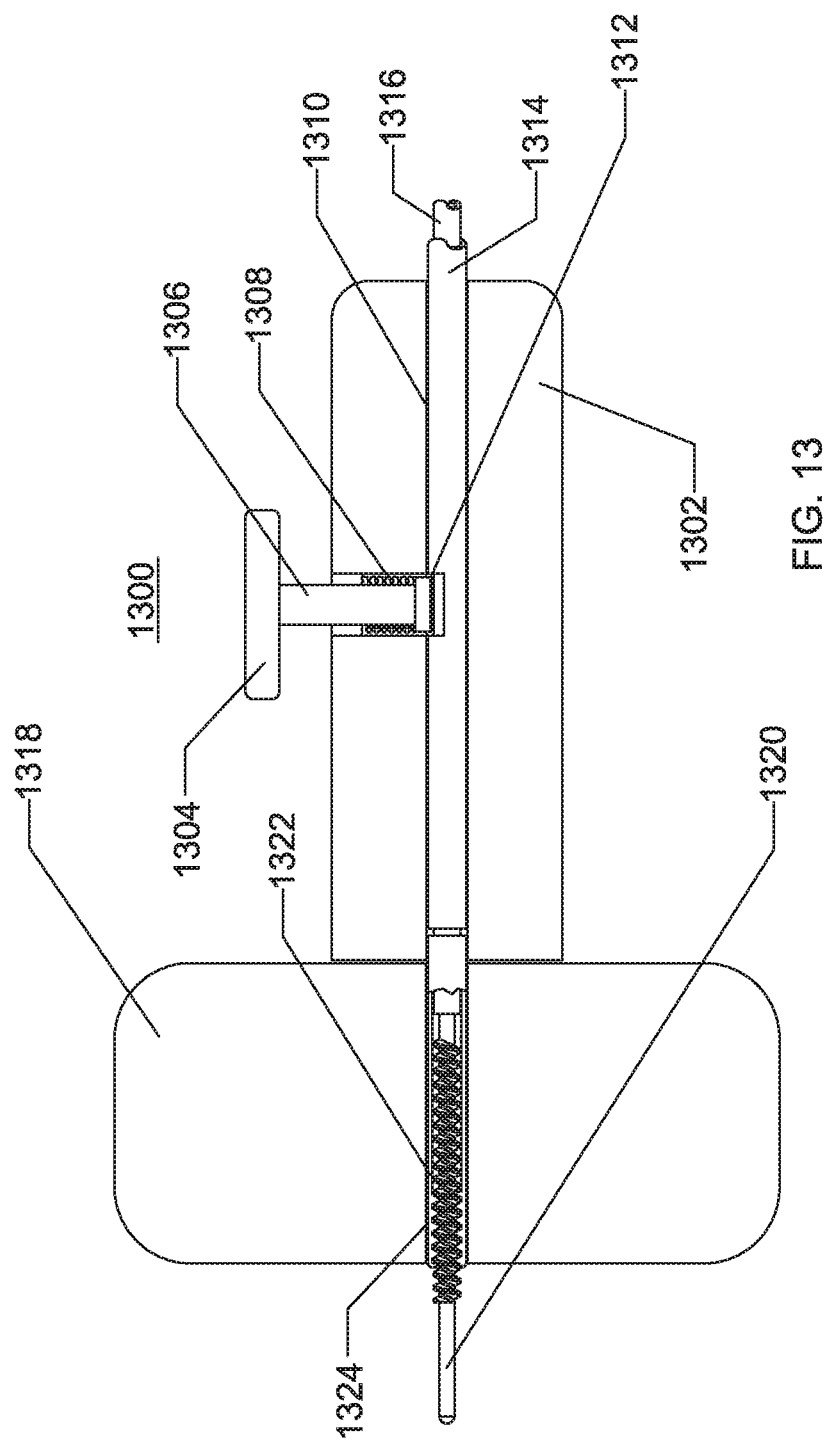
FIG. 13 illustrates a side, cutaway view of the hub of a steerable guidewire showing a pin system to engage the outer tube and an engagement between the control knob and a jackscrew affixed to the inner tube of the guidewire.

FIG. 13 illustrates a side view, in cross-section, of the proximal end of a steerable guidewire 1300 comprising a hub body 1302, a release control 1304, a release control pin 1306, a spring 1308, a hub lumen 1310, an outer tube lock window 1312, an outer tube 1314, an inner tube 1316, a control knob 1318, further comprising jackscrew traveler engagement features 1324, a jackscrew 1320, and a jackscrew traveler 1322.

The hub body 1302 is releasably affixed to the outer tube 1314 by engagement of the release control pin 1306 with the window 1312. The release control pin 1306 is affixed to or integral with a button 1304 that permits a user to grab or the pin and pull or push the button down. The spring 1308 pushes or biases the release control pin 1306 radially inward. The hub body 1302 comprises a lumen through which the outer tube 1314 is longitudinally, slidably engaged. The control knob 1318 is constrained to rotate about the longitudinal axis of the hub body 1302 but cannot move in the longitudinal or axial direction. The interior lumen of the control knob 1318 comprises jackscrew engagement features, in this case, a rectangular opening sized to slidably accept the flat sided jackscrew traveler exterior. This engagement could be a key, pin and slot, or the like. The inner tube 1316 slides longitudinally within the outer tube 1314 but is radially constrained therein.

The hub body 1302, the control knob 1318, the release control pin 1306, the release pin button 1304 can all be fabricated from metal, plastic, ceramic, or the like. The spring 1308 can be a coil spring, leaf spring, or the like. The spring 1308 can also comprise a magnet polarized so as to attract metallic components of the locking pin 1306 or button 1304 inward toward the window 1312.

FIG. 14A illustrates a side view, in partial cross-section or breakaway, of the proximal end of the steerable guidewire 1300 with the hub removed. The proximal end of the steerable guidewire 1300 comprises the jackscrew 1320, the jackscrew traveler 1322 further comprising a threaded region 1414 and a control knob engagement feature 1416, the outer tube 1314, further comprising the window 1312, and the inner tube 1316.

The jackscrew 1320 and the jackscrew traveler 1322 can be fabricated from stainless steel, titanium, nitinol, cobalt nickel alloy, or the like. The jackscrew 1320 can have a thread ranging from about 24 threads per inch to about 80 threads per inch with a preferred range of about 28 to about 56 threads per inch. Jackscrew traveler 1322 comprises threads that are complimentary to those on the jackscrew 1320 such that rotation of the jackscrew traveler 1322 causes the jackscrew traveler to move axially relative to the jackscrew 1320.

The jackscrew 1320 is press-fit, welded, or otherwise affixed to the inner tube 1316 and is immovable with respect to the inner tube.

FIG. 14B illustrates a lateral cross-sectional view of the jackscrew 1320 and the jackscrew traveler 1322 further comprising the control knob engagement mechanism 1416, which comprises a plurality of external flat surfaces 1418.

The flats 1418 are configured to engage a rectangular or square opening on the inside of the control knob of FIG. 13.

FIG. 14C illustrates a side view of the jackscrew 1320 further comprising a proximal lead-in 1414, an external thread 1410, and an inner tube engagement and fastening pin 1408.

The jackscrew 1320 comprises a lead-in 1414 which is tapered at its proximal end to facilitate threading catheters over it. The distal end of the jackscrew 1320 comprises a pin 1408 which is inserted into the inner tube 1316 for alignment and can be used to weld, bond, or lock the inner tube to the jackscrew 1320. In an alternative embodiment, the jackscrew traveler element may be affixed to the proximal end of the outer tube, and the jack-screw traveler element may comprises a traveler thread, and the outer tube can be tensioned axially relative to the hub and the inner tube in response to movement of the jack-screw traveler element. Also, the internal lumen of the hub may be configured to receive the jack-screw traveler element and prevent the jack-screw traveler element from rotating about the longitudinal axis of the hub, in which case the inner tube is constrained not to move relative to the hub; and the knob may be affixed to the hub and capable of being rotated by a user, and the knob may comprises a knob thread such that the knob thread and the jackscrew traveler thread engage.

FIG. 15A illustrates side view, in partial cross-section, of the proximal end of a steerable guidewire 1500. The steerable guidewire 1500 comprises an outer tube 1502, an inner tube 1504, a first inner tube locking collar 1506, a second inner tube locking collar 1508, a tube lock subassembly 1518 further comprising a locking pin 1510, a locking pin spring 1512, an outer tube opening 1514, and an inner tube opening 1516.

The lock subassembly 1518 can be configured to slide within the lumen of the inner tube 1504 until the pin 1510 is pushed outward through the inner tube window 1516 by the spring 1512. The locking pin spring can be a cantilever spring, as illustrated, or it can be a coil spring or even a magnetically outwardly biased structure. The window 1514 in the outer tube 1502 is beneficially sized a little bit bigger than the window 1514 in the inner tube 1504 to facilitate locating the hole in the outer tube 1502. Alignment marks (not shown) or keys (not shown) can be used to maintain rotational alignment between the inner and outer tubes thus, facilitating engaging the locking pin 1510 with the outer tube window 1514. The locking collars 1506 and 1508 can be fabricated from metal (preferred) or plastic. The locking collars 1506 and 1508 can be welded, bonded, or fastened to the inner tube 1504 so as to be affixed thereto. They can be used in conjunction with the locking pin 1316 in the hub of FIG. 13 to provide for an easy axial lock that functions independent of rotational orientation between a hub and the inner tube 1504.

FIG. 15B illustrates a lateral cross-section of the region around the tube lock subassembly 1518 of FIG. 15A, comprising the locking pin 1510, the outer tube 1502, the inner tube 1504, the locking pin spring 1512, the inner tube opening 1516, and the outer tube opening 1514.

This view in the direction of the axis of the system illustrates how the locking system 1518 can be inserted into the lumen of the inner tube 1504 and moved to a location where the pin 1510 snaps out through the window 1516 of the inner tube 1504.

FIG. 16A illustrates a side view, in partial cross-section of the proximal end of a steerable guidewire 1600 comprising an inner tube 1604, an outer tube 1602, a plurality of leaf spring catches 1606, a first locking collar 1506 and a second locking collar 1508.

The leaf spring catches 1606 can be cut into the inner tube using a laser cutter or other machining system with small cut width. These leaf spring catches 1606 can be, then, yielded outward until their outward extent approximates that of the outer tube 1602 outer diameter. These leaf spring catches 1606 are now biased to spring outward, if not restrained. There is no window needed in the outer tube 1602 as long as the tubes are biased to move toward each other but a window (not shown) can be generated in the outer tube to engage with the leaf spring catches 1606 to prevent tensile motion pulling the inner tube 1604 from the outer tube 1602. The two leaf spring catches 1606 seen on the side of the inner tube 1604 opposite the four leaf spring catches 1606 can be used to increase resolution and reduce the size of the increments between latching locations. Leaf spring catches 1606 can be oriented in either direction along the axis of the inner tube 1604 to provide for locking with respect to either compression or tensile forces (or both) acting between the inner 1604 and outer tube 1602.

FIG. 16B illustrates a top view of the steerable guidewire 1600 comprising the outer tube 1602, the inner tube 1604, the spring catches 1606, the first locking collar 1506 and the second locking collar 1508. The inner tube 1604 can be fabricated from spring temper stainless steel such as 304 SS or 316 SS.

FIG. 17 illustrates a side view, in partial cross-section, of a steerable guidewire 1700 comprising the outer tube 1602, the inner tube 1604, the plurality of spring catches 1606, a hub body 1702 further comprising a lumen 1712, a control knob 1704 further comprising internal threads (not shown), a releasable lock 1706, and a jackscrew traveler (not shown) further comprising an outer tube pusher 1710.

The hub can be fabricated from the same materials as those of the hub in FIG. 13. The jackscrew traveler (not shown) and the outer tube pusher 1710 can be fabricated from stainless steel, cobalt nickel alloy, titanium, or the like. The outer tube pusher 1710 can be configured to push the leaf spring catches 1606 radially inward to cause them to release. This can be selective controlled or occur when the outer tube pusher 1710 rides over the exterior of the leaf spring catches 1606.

FIG. 18 illustrates a side view of a steerable guidewire comprising a straight portion of tubing 1820, a bendable portion of tubing 1826, a control knob 1824, a hub body 1822 and a catheter 1800 configured to ride alongside the steerable guidewire. The catheter 1800 comprises a catheter shaft 1802, a dilator 1806 further comprising a dilator tip 1814, a catheter hub 1804, a dilator hub 1808, a first rail lock 1810, and a second rail lock 1812.

The first rail lock 1810 and the second rail lock 1812 are illustrative. There can be only one rail lock or there may two or more rail locks. The rail locks 1810 and 1812 can be configured as spring-loaded C-clamps that spread apart and then re-close around the steerable guidewire exterior. The rail locks 1810, 1812 can also be configured as carabiner, which have closures, or simple loops that do not open. The rail locks 1810 and 1812 are configured to be movable in the axial direction over the exterior of the steerable guidewire but not permit the catheter 1800 to release from the steerable guidewire except when desired and under the control of an operator. The distal tip 1814 can be configured to be symmetrical or it can be configured asymmetrically and tapered toward the side of the rail locks 1810, 1812, as illustrated. In this embodiment, the hub 1822 and control knob 1824 do not have to be removed from the steerable guidewire in order to use the steerable guidewire as a track to advance a catheter to a target site.

Figure 19:
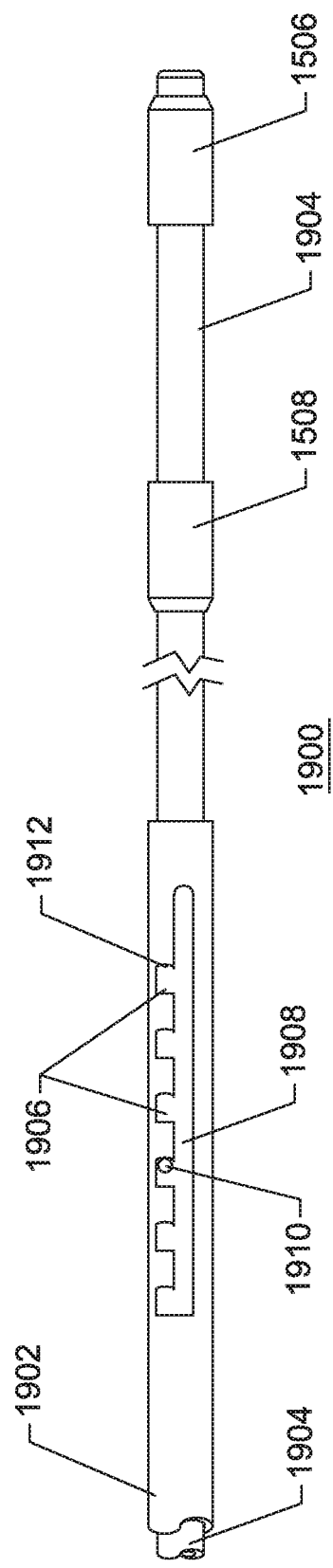
FIG. 19 illustrates the proximal end of a steerable guidewire comprising an outer tube with a longitudinal slot with a plurality of cul-de-sacs and an inner tube or rod comprising a pin or protrusion that mates or engages with the cul-de-sacs and slides axially within the longitudinal slot, wherein the pin or protrusion is shown within one of the cul-de-sacs.

FIG. 19 illustrates the proximal end of a steerable guidewire 1900 comprising an outer tube 1902 further comprising a longitudinal slot 1908 opening to one or more circumferential slots or cul-de-sacs 1906. The steerable guidewire 1900 also comprises a protrusion 1910 on the exterior of the inner tube or rod 1904, such that the protrusion 1910 is oriented substantially radially outward, and further wherein the protrusion 1910 is sized to slide axially within the longitudinal slot 1908 in the wall of the outer tube. The protrusion 1910 is further sized to engage with the cul-de-sacs 1906 to lock the two tubes 1902 and 1904 against relative longitudinal or axial movement. The one or more cul-de-sacs 1906 can further comprise depressions 1912 that can prevent inadvertent dislodgement of the protrusion, especially given a small or large amount of spring bias created by deformation at the distal end of the steerable guidewire 1900. Since the inner tube or rod 1904 and outer tube 1902 are long, a small amount of circumferential movement relative to each other is quite possible and easily achieved with manual or mechanical force. The positions of the inner tube or rod 1904 and outer tube 1902 can be arranged such that a rotational spring bias is imposed causing the protrusion to preferentially position itself within one of the cul-de-sacs 1906. Removal of the protrusion 1910 from the cul-de-sac 1906 can require circumferential reverse rotation or a bit of axial movement first to move the protrusion 1910 out of any depressions 1912 within the cul-de-sac 1906. Thus the inner tube 1904 and outer tube 1902 can be releasably locked relative to each other at one or more discreet locations. This structure is preferably located at or near the proximal end of the steerable guidewire 1900. The inner tube 1904 further comprises the latching features 1506 and 1508.

Instead of having the inner tube or rod cut into a control rod and a keeper or stay, the stay or keeper can be eliminated and the inner tube or rod separated into two or more control rods that can be affixed to the apparatus at a point distal to the bendable region. The proximal ends of the control rods extend all the way into the hub and are affixed to separate actuators, which can be jackscrews, hydraulic actuators, pneumatic actuators, magnetic actuators, or the like. Since the distal end of the device can have various bending characteristics and symmetry, it is beneficial that each control rod have a separate actuator that can move at different axial distances given a single control input by the user. For example, two jackscrews can comprise different thread pitches to accommodate off-center motion at the distal bendable region. Thus a push-pull force balance is applied to the distal end to enhance the amount of flexural modulus and increase the bending forces that can be generated by the system. Control rods that are not used or actuated at the proximal end can serve as keepers or stays to maintain the radial position of the control rods in an off-center configuration.

The embodiments presented herein describe a system that does not use pull wires. No side lumens are required in either the outer tube or the inner tube. Such side lumens, as found in certain prior art catheters, require extensive cross-sectional area be used to surround the side lumens and take away from the potential area for the central lumen since the outside extent of the catheter is limited. The use of pull wires requires such as those in certain prior art catheters, retaining these structures along one side of the outer tube may be difficult or impossible. Side lumens or channels are necessary to retain a pull wire or control rod in the correct location so as to provide correct off center forces to bend the distal end. The side lumens are also necessary to keep the control rod or pull wires out of the central lumen which needs to remain open and substantially circular. The system disclosed herein, however, retains a high degree of column strength, maximum torqueability, the largest possible central lumen, and a very strong control and steering function or capability. Furthermore, the side lumens or channels are necessary to maintain spatial (rotational orientation) for the articulating distal end of the device. Without the side lumens or channels permitting axial slidability but generating radial retention, the pull wires or pushrods would be free to migrate around within the central lumen of the device and could bend the device in an unwanted direction. Long guidewires with relatively small cross-sectional areas are highly subject to torque and rotational misalignment and some method must be employed to retain the correct circumferential location of the articulating apparatus.

Furthermore, a pull-wire as used in prior art devices is incapable of generating compression against the distal end of the device so a pull-wire could not, under compression, move or articulate the distal end of the device. The pull-wire, under tension, can move or articulate the distal end and would require some sort of counterforce such as an opposing pull-wire, shape memory metal, or spring return biasing to move the distal end in the reverse direction.

However, a tubular or cylindrical (substantially no lumen) central control device can maintain its structure in compression, maintain circumferential location within the outer cylindrical, axially elongate tube, maintain precise control, maintain sufficient tensile strength to exert forces, and maintain a central lumen larger than any other type of steerable device. The resistance to buckling occurs even when the inner tube is slotted longitudinally because the inner tube is constrained within the outer tube using very tight tolerances that will not let the inner tube bend out of its straight orientation, even under compression.

The hub of the steerable guidewire can comprise hard stops or disengagement features, preferably reversible so that re-engagement of the jackscrew can occur, that prevent the jackscrew or other control mechanism from exerting excessive forces within the hub or guidewire.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A method of steering a luminal access device into a body lumen, tissue, or cavity of mammalian body comprising the steps of:
    inserting the luminal access device into the body lumen, tissue, or cavity and routing the luminal access device to a target site, wherein the luminal access device comprises an inner tube, an outer tube, a bendable region near a distal end of the luminal access device and a hub that comprises a control element at a proximal end on the luminal access device,
    deflecting the bendable region near the distal end of the luminal access device into a curved configuration, wherein the deflecting step is performed by applying force by the control element on the proximal end of the luminal access device,
    locking the luminal access device such that when the hub is removed, the bendable region is maintained in the curved configuration;
    removing the hub of the luminal access device, and thereafter advancing a catheter over the curved luminal access device to the target site while the bendable region is in the curved configuration.

2. The method of claim 1 wherein the step of locking the luminal access device comprises longitudinally fixing the inner tube to the outer tube at a point proximal to the bendable region.

3. The method of claim 1 wherein the step of locking the luminal access device comprises longitudinally fixing the inner tube to the outer tube at a point proximal to the bendable region by allowing an element longitudinally fixed to the inner tube to penetrate an aperture in the outer tube.

4. The method of claim 1 wherein the deflecting step comprises operating the control element to tension or compress the inner tube relative to the outer tube, or tension or compress the outer tube relative to the inner tube.

5. A method of steering a first luminal access device into a body lumen, tissue, or cavity of mammalian body comprising the steps of:
- inserting the first luminal access device into the body lumen, tissue, or cavity and routing the first luminal access device to a target site, wherein the first luminal access device comprises an inner tube, an outer tube, a bendable region near a distal end of the first luminal access device and a hub that comprises a control element at a proximal end on the first luminal access device;
- deflecting the bendable region near the distal end of the first luminal access device into a curved configuration, wherein the deflecting step is performed by applying force by the control element on the proximal end of the first luminal access device;
- locking the first luminal access device such that when the hub is removed, the bendable region is maintained in the curved configuration;
- removing the hub of the first luminal access device; and thereafter
- advancing a second luminal device through the first luminal access device to the target site while the bendable region is in the curved configuration.

6. The method of claim 5 wherein the step of locking the first luminal access device comprises longitudinally fixing the inner tube to the outer tube at a point proximal to the bendable region.

7. The method of claim 5 wherein the step of locking the first luminal access device comprises longitudinally fixing the inner tube to the outer tube at a point proximal to the bendable region by allowing an element longitudinally fixed to the inner tube to penetrate an aperture in the outer tube.

8. The method of claim 5 wherein the step of locking the first luminal access device comprises longitudinally fixing the inner tube to the outer tube at a point proximal to the bendable region.

9. The method of claim 5 wherein the step of locking the first luminal access device comprises longitudinally fixing the inner tube to the outer tube at a point proximal to the bendable region by allowing an element longitudinally fixed to the inner tube to penetrate an aperture in the outer tube.

10. The method of claim 5 wherein the deflecting step comprises operating the control element to tension or compress the inner tube relative to the outer tube, or tension or compress the outer tube relative to the inner tube.

11. A method of steering a first luminal access device into a body lumen, tissue, or cavity of mammalian body comprising the steps of:
- inserting the first luminal access device into the body lumen, tissue, or cavity and routing the first luminal access device to a target site, wherein the first luminal access device comprises an inner tube formed into at least one control rod at its distal end, an outer tube, a bendable region near a distal end of the first luminal access device and a hub that comprises a control element at a proximal end on the first luminal access device;
- deflecting the bendable region near the distal end of the first luminal access device into a curved configuration, wherein the deflecting step is performed by applying force by the control element on the proximal end of the first luminal access device;
- locking the first luminal access device such that when the hub is removed, the bendable region is maintained in the curved configuration; and thereafter
- removing the hub of the first luminal access device.

12. The method of claim 11 wherein the deflecting step comprises operating the control element to tension or compress the inner tube relative to the outer tube, or tension or compress the outer tube relative to the inner tube.

\* \* \* \* \*